(12) United States Patent
Laurence et al.

(10) Patent No.: US 10,098,327 B2
(45) Date of Patent: *Oct. 16, 2018

(54) CORE-TEMPERATURE-BASED HERD MANAGEMENT SYSTEM AND METHODS

(71) Applicant: HERDX, INC., San Antonio, TX (US)

(72) Inventors: Laird W Laurence, Fredericksburg, TX (US); James Derwin King, San Antonio, TX (US); James C Lyman, Pipe Creek, TX (US); Jack C Laurence, San Antonio, TX (US); Michael R Williams, Fredericksburg, TX (US); Allen Nance, Fredericksburg, TX (US); Ronald B Hicks, Boerne, TX (US)

( * ) Notice: Subject to any disclaimer, the term of this patent is extended or adjusted under 35 U.S.C. 154(b) by 182 days.

This patent is subject to a terminal disclaimer.

(21) Appl. No.: 13/685,273

(22) Filed: Nov. 26, 2012

(65) Prior Publication Data

US 2013/0239907 A1    Sep. 19, 2013

Related U.S. Application Data

(63) Continuation of application No. 12/644,050, filed on Dec. 22, 2009, now Pat. No. 8,317,720.

(60) Provisional application No. 61/203,606, filed on Dec. 24, 2008.

(51) Int. Cl.
| | |
|---|---|
| *A01K 29/00* | (2006.01) |
| *A61B 5/01* | (2006.01) |
| *A61M 5/172* | (2006.01) |
| *G06F 19/00* | (2018.01) |
| *A61D 7/00* | (2006.01) |

(52) U.S. Cl.
CPC ............. *A01K 29/00* (2013.01); *A61B 5/01* (2013.01); *A61D 7/00* (2013.01); *A61M 5/1723* (2013.01); *G06F 19/3418* (2013.01); *A61B 2503/40* (2013.01); *A61M 2230/50* (2013.01); *A61M 2250/00* (2013.01)

(58) Field of Classification Search
CPC ...... A01K 11/006; A61B 5/01; A61B 2503/40
See application file for complete search history.

(56) References Cited

U.S. PATENT DOCUMENTS

| | | | | |
|---|---|---|---|---|
| 3,299,274 A | * | 1/1967 | Hoelter | 356/217 |
| 3,491,596 A | * | 1/1970 | Dean | 374/178 |
| 3,650,058 A | * | 3/1972 | Wittcke | G09F 11/23 40/300 |
| 3,781,837 A | * | 12/1973 | Anderson et al. | 600/549 |
| 4,274,083 A | * | 6/1981 | Tomoeda | 340/13.25 |
| 4,797,840 A | * | 1/1989 | Fraden | 702/104 |
| 4,854,328 A | * | 8/1989 | Pollack | 600/549 |
| 4,865,044 A | * | 9/1989 | Wallace et al. | 600/549 |

(Continued)

*Primary Examiner* — Sean Dougherty
(74) *Attorney, Agent, or Firm* — Jackson Walker LLP

(57) ABSTRACT

A system and method for managing a herd of animals possibly requiring medical treatment, such as cows in a feedlot. The animals are herded individually into a chute, where identification data is collected from a tag, and core temperature data is collected using a special non-contacting core temperature sensor. The animal is tagged with a color coded tag representing a range of temperatures into which that animal's temperature falls. The animal is then delivered to a pen corresponding to that range of temperatures, where appropriate medicinal treatment is automatically dosed and applied to the animal.

30 Claims, 9 Drawing Sheets

(56) References Cited

U.S. PATENT DOCUMENTS

| | | | | |
|---|---|---|---|---|
| 5,110,200 A * | 5/1992 | Snook | | 351/212 |
| 5,115,815 A * | 5/1992 | Hansen | | 600/474 |
| 5,331,923 A * | 7/1994 | Mollhagen | A01K 1/0613 | 119/729 |
| 5,673,647 A * | 10/1997 | Pratt | A01K 1/0023 | 119/51.02 |
| 5,811,811 A * | 9/1998 | Naya | | 250/339.15 |
| 5,813,982 A * | 9/1998 | Baratta | | 600/398 |
| 5,959,526 A * | 9/1999 | Tucker | A01J 5/0175 | 119/14.03 |
| 6,312,393 B1 * | 11/2001 | Abreu | | 600/558 |
| 6,346,885 B1 * | 2/2002 | Curkendall | | 340/572.4 |
| 6,613,179 B1 * | 9/2003 | McCoy | B32B 38/14 | 156/277 |
| 6,773,405 B2 * | 8/2004 | Fraden et al. | | 600/549 |
| 6,868,804 B1 * | 3/2005 | Huisma et al. | | 119/842 |
| 6,892,671 B1 * | 5/2005 | Miyawaki | A01K 29/00 | 119/174 |
| 7,026,939 B2 * | 4/2006 | Letkomiller et al. | | 340/572.7 |
| 7,129,423 B2 * | 10/2006 | Baarsch | A01K 1/0023 | 119/842 |
| 7,334,938 B2 | 2/2008 | Remsburg | | 374/109 |
| 7,335,168 B2 | 2/2008 | Rugg | | 600/595 |
| 7,467,603 B2 * | 12/2008 | Davies | | 119/712 |
| 7,522,059 B1 | 4/2009 | Kleemeier | | 340/573.3 |
| 7,616,124 B2 * | 11/2009 | Paessel et al. | | 340/573.3 |
| 7,705,736 B1 | 4/2010 | Kedziora | | 340/573.3 |
| 8,019,633 B2 * | 9/2011 | Stroman | G06Q 10/063 | 705/7.11 |
| 8,298,148 B2 * | 10/2012 | Furman | | 600/453 |
| 8,331,888 B2 * | 12/2012 | Halladay et al. | | 455/187.1 |
| 8,398,560 B2 * | 3/2013 | Elser | | 600/534 |
| 8,866,605 B2 * | 10/2014 | Gibson | | 340/539.1 |
| 2002/0010390 A1 * | 1/2002 | Guice | A01K 11/008 | 600/300 |
| 2002/0115915 A1 * | 8/2002 | Pratt | A01K 5/02 | 600/300 |
| 2002/0116200 A1 * | 8/2002 | Cureton | A01K 5/02 | 705/1.1 |
| 2003/0140865 A1 * | 7/2003 | Fuqua | A01K 11/004 | 119/174 |
| 2003/0142723 A1 * | 7/2003 | Laurence et al. | | 374/121 |
| 2004/0240517 A1 * | 12/2004 | Howard | | 374/130 |
| 2005/0145187 A1 * | 7/2005 | Gray | A01K 11/008 | 119/174 |
| 2005/0217590 A1 * | 10/2005 | Martinez | A01K 11/005 | 119/51.02 |
| 2005/0223997 A1 * | 10/2005 | Umegard | A01K 1/12 | 119/14.03 |
| 2005/0267344 A1 * | 12/2005 | Woods et al. | | 600/316 |
| 2006/0017883 A1 * | 1/2006 | Dai et al. | | 351/205 |
| 2006/0054092 A1 * | 3/2006 | Valencia | A01K 29/00 | 119/51.02 |
| 2006/0178579 A1 * | 8/2006 | Haynes | A61B 8/08 | 600/437 |
| 2006/0185605 A1 * | 8/2006 | Renz | A01K 29/00 | 119/51.02 |
| 2006/0201432 A1 * | 9/2006 | Pratt | A01K 29/00 | 119/51.02 |
| 2007/0044732 A1 * | 3/2007 | Araki | A01K 11/008 | 119/721 |
| 2007/0258625 A1 * | 11/2007 | Mirtsching | A22B 5/007 | 382/110 |
| 2008/0030348 A1 * | 2/2008 | Pape et al. | | 340/573.3 |
| 2008/0059534 A1 * | 3/2008 | Stroman et al. | | 707/104.1 |
| 2008/0194983 A1 * | 8/2008 | Laurence | G01J 5/0022 | 600/549 |
| 2008/0314325 A1 * | 12/2008 | Hempstead | A01K 11/006 | 119/51.02 |
| 2009/0145364 A1 * | 6/2009 | Hardy | A01K 1/0613 | 119/14.04 |
| 2010/0170446 A1 * | 7/2010 | Manneke | A01K 1/0047 | 119/14.02 |
| 2010/0180824 A1 * | 7/2010 | Bright | A01K 1/0023 | 119/14.08 |

* cited by examiner

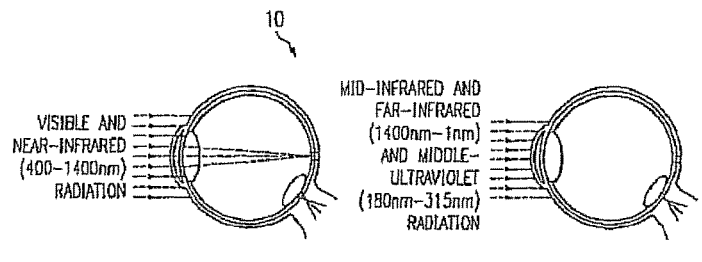
*Figure 10*
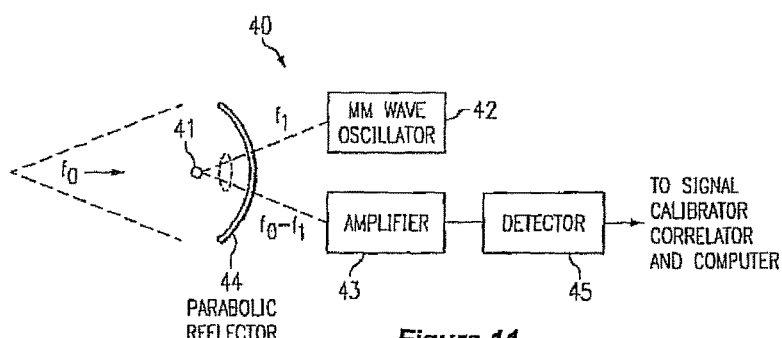
*Figure 11*
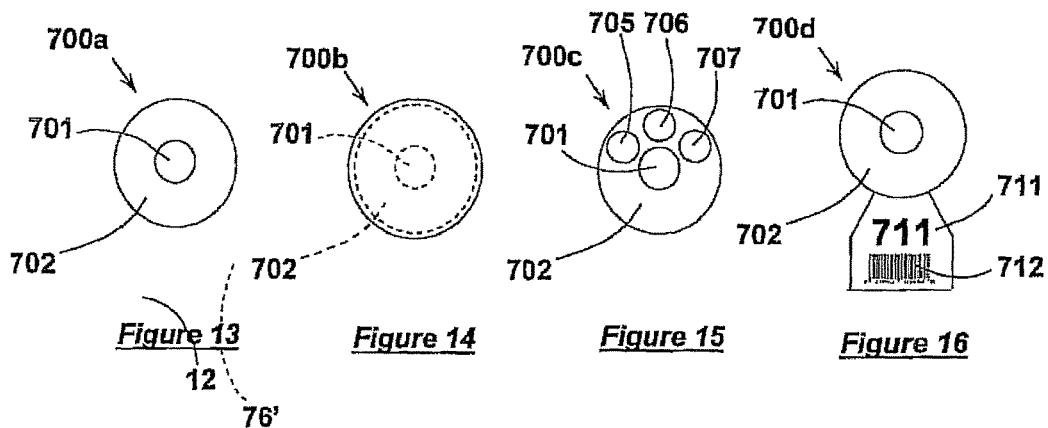
*Figure 13*   *Figure 14*   *Figure 15*   *Figure 16*

CORE-TEMPERATURE-BASED HERD MANAGEMENT SYSTEM AND METHODS

CROSS-REFERENCE TO RELATED APPLICATIONS & PATENT

This application is a continuation of U.S. patent application Ser. No. 12/644,050, filed Dec. 22, 2009, issued as U.S. Pat. No. 8,317,720 on Nov. 27, 2012, which claims the benefit of and filing date priority from U.S. Provisional Application No. 61/203,606, filed Dec. 24, 2008, and entitled "CORE-TEMPERATURE-BASED HERD MANAGEMENT SYSTEMS & METHODS." The contents of these prior applications are incorporated by reference herein in their entirety.

Portions of this application and its subject matter are related to pending U.S. patent application Ser. No. 11/971,088, entitled "MEANS AND APPARATUS FOR RAPID, ACCURATE, NON-CONTACTING MEASUREMENT OF THE CORE TEMPERATURE OF ANIMALS AND HUMANS," filed Jan. 8, 2008, as well as to U.S. Pat. No. 7,336,987, entitled "METHOD AND APPARATUS FOR RAPID, NON-CONTACT MEASUREMENT OF THE CORE TEMPERATURE OF ANIMALS AND HUMANS," dated Feb. 26, 2008, the contents of each of which are incorporated herein by this reference in their entirety.

TECHNICAL FIELD

This invention relates in general to management of livestock herds and, more particularly, to comprehensive systems and methods for managing and tracking livestock herds based at least in part on instantaneous temperature or other health assessments of individual members of the herd.

BACKGROUND OF THE INVENTION

Feeding facilities (a/k/a feedlots or feed yards) are critical to the world's food supply, but managing them efficiently presents many challenges. For example, upon arrival at a typical cattle feedlot, each member of the herd will make at least one trip through a chute, where handlers can typically afford to spend only about 45-seconds processing each calf. Initial processing typically involves some variation of each of the following: (1) standard treatment such as spraying, deworming, and whatever type of basic treatment is being administered to the entire herd; (2) when feasible, some level of assessment and any special treatment that may be indicated based on the assessment; and (3) identification by attaching either an RFID ear tag, a numbered or bar-coded ear tag, or some other form of individual animal identification. Other processing activities can include vaccination, castration, horn-tipping, weighing, etc., all of which can help in managing the herd. Naturally, whatever processing takes place, records also need to be created, updated and transferred for each calf being processed.

Challenges arise from the need for speed while it is so difficult to determine what particular type of treatment is needed for each individual calf. Yet, when a feedlot omits a critical treatment, it can lose a big part of the herd . . . fast. So, rather than attempt to predict which calves need treatments and which do not, the industry is constantly facing temptations to mass treat all animals entering their lot as a precaution. Mass antibiotic treatment of an entire herd of 'at risk' cattle is not only expensive, but it presents a litany of concerns for beef quality and microbial mutation. Regulatory agencies (e.g., FDA) strongly discourage overuse of antibiotics in order to minimize the risk of microbial mutation, practically outlawing Gentamicin Sulphate and blended cocktail treatments for use in bovine applications. Plus, while most consumers would rather consume pure organic beef cattle with fewer additives, there has long been a huge need to improve herd processing through more accurate assessments and more intelligent treatments.

Other herd management practices have been advancing more systematically than livestock assessment techniques, particularly in the area of livestock tagging. Tags applied to each calf are used to identify the particular calf and are typically applied in the ear where they can be readily seen and tracked. Radio Frequency Identification ("RFID") technology is being utilized to a greater extent in the agricultural industry. More and more historical data is being required by regulatory agencies before a calf can be slaughtered or packed.

At least one other company has attempted to help ranchers manage cattle based on temperature, but its attempt has been less than ideal. Tekvet [website: tekvet.com] has launched a system of mobile temperature monitors (mounted in the calves' ears) which link to a base station. It is an object of the present invention to improve over such prior attempts, providing a system that provides a more accurate temperature measurement that is more consistently reliable, and more cost effective than a surface-based thermistor mounted in the ear.

Core temperature, the internal body temperature, or more precisely the temperature of the blood as it flows in or near the pulmonary artery near the heart, would be even more ideal. Unfortunately, core temperature has been difficult to measure accurately without invasive placement in the sensitive interior of the body. Such measurements have long required a surgically invasive insertion of a temperature probe, which is impractical for use in feedlots. In practice, core temperature is not really measured but is approximated with rectal, oral and ear thermometers and others. A better, more accurate and more rapid non-invasive measurement of actual core temperature is needed for use in the field.

In the United States' cattle industry, annual mortality of cattle due to disease is estimated to be in the hundreds of millions of dollars. A reliable method of determining the health of a calf or the presence of disease is by assessing the body temperature of the animal. In the case of infections, environmental factors, or toxins, a calf's temperature will elevate. These elevations are diagnostic to veterinarians in the diagnosis of disease and disease conditions in cattle. In the day-to-day production of cattle, the evaluation of the presence of increased body temperature or fever is under utilized due to time constraints and the need to physically restrain the animal. This under utilization of temperature evaluation delays the diagnosis of disease and therefore increases the ineffective uses of medications and loss of animals.

Traditionally, to obtain temperature measurements, clinical thermometers have been inserted rectally or orally and must remain in position for periods of as long as several minutes to obtain a stable reading. This usually requires restraint of the animal, which is time consuming and labor intensive. Typically, the body temperature of cattle is measured with a clinical mercury Fahrenheit thermometer or with a digital thermometer. A mercury thermometer has a scale ranging from 94 F. to 110 F. and each degree is divided into ⅕ths. The thermometer requires shaking the mercury column into the bulb end. The thermometer is then lubricated or moistened and manually inserted its full length into the rectum. It remains in the rectum for a minimum of 3 minutes to obtain an accurate reading. As most animals object to this procedure, the animal must be physically restrained during this time.

In recent years, temperature sensors of low thermal mass, such as miniature thermocouples or thermistors, have been used with an electronic digital readout to make the more rapid digital thermometers. However, these devices still require oral or rectal insertion and restraint of the animal but the time for accurate measurement is reduced to one minute.

Other approaches to animal temperature measurement are based on sensing the thermal emission energy, the so called black body emission. This energy is emitted as a wide band electromagnetic spectrum by all heated bodies and has a wavelength distribution and intensity in proportion to temperature. This emitted energy is detected by use of a non-contact microwave, millimeter (mm) wave, or infrared (IR) sensors. Thermal emission measurement is rapid, but the accuracy by which the thermal emission is related to temperature is affected by two factors, in addition to instrumental errors, if any. The first factor is how accurately an emitting surface that is accessible for measurement relates to the core temperature. This frequently poses a problem in that skin may not be a true representation of the internal temperature. This is particularly a problem with Infrared (IR), where the depth within a body from which the emission is detected is very shallow and is essentially proportional to the outer temperature of the skin.

The second factor, surface emissivity, also affects the amount of thermal emission from a body at a given temperature. This causes temperature measurements, based on thermal emissions, to vary depending on the color and the physical properties of the materials being measured. To attempt to overcome this source of error, some IR thermal emission thermometers use a probe inserted into the ear. However, surface emissivity in the ear can vary due to the amounts and types of debris and these can limit the accuracy. In another variation, an insert is placed in the ear of the animals to provide a constant emissivity target for the IR sensor. The insert must be in the ear for a sufficient time to reach thermal equilibrium prior to measurement, which is undesirable from cost and time considerations.

The possibility of measuring the core temperature of cattle by remote (hands-off) sensing has been of great interest over the past thirty years or more. Previous approaches have been based on (1) passive detection of the magnitude of the IR or microwave energy that is emitted in proportion to the temperature and wavelength (in accordance with Planck's law) from most materials including human or animal hide or ear (interior); (2) the use of implants and/or tags which use contact type•thermal sensors (thermistors, thermocouples, etc.) and usually a wireless means of reading out the data on demand; and (3) the use of ingested temperature sensing capsules which contain a temperature sensor and a radio frequency (VHF or UHF) transmitter or transponder to communicate the temperature data from the interior of the animal to an outside read out unit. None of these previous devices or approaches is completely satisfactory due to cost, poor accuracy, practical application limitations, or other reasons.

Existing passive IR emission thermometers are of limited accuracy (+/−one degree or worse). These methods are based on sensing surface (skin or hide) temperature and do not have sufficient accuracy nor repeatable for direct measurement of animal body temperature. Skin temperature is not always an accurate indication of the internal temperature of the animal. Also, the emissivity of hair-covered skin is variable and, with IR, will not provide accurate skin temperature nor core temperature indications.

SUMMARY OF THE INVENTION

The present invention is just the answer for many of the unmet needs that have plagued the livestock industries—allowing efficient management of a herd based on quick assessment of core temperature in less than five seconds while each calf is in the chute. Other features also allow selective administration of appropriate antibiotics to calves categorized in subclinical and clinical symptom groups. Sorting and tagging the herd correspondingly further allows for practical control of various aspects of down stream management. The result enables not only early intervention for calves that actually need antibiotics, but also informed management of the overall herd based on objective standards. More importantly to the feedlot, the preferred embodiments enable increased feedlot profitability and potential cost savings.

A sizable, unmet need has been revealed in relation to optimizing livestock treatment, particularly with antibiotics and other pharmaceutical treatments. Related needs include the goal to minimize unnecessary treatment of livestock and to avoid over-treatment of livestock that are not likely to benefit from such treatment, or that may fare better without such treatment. It is an object of the present invention to address these and other needs presented by the prior art. By enabling more intelligent assessment of livestock—thereby enabling identification and appropriate treatment of livestock that would likely need some form of treatment. Other objects include enabling such predicted, appropriate treatment while not treating (or while reducing or modifying the treatment for) those that are less likely to benefit.

Overriding objects of the present inventions also include providing herd management systems and methods that facilitate and adjust, based on a reliable yet rapid health indicator. A related object includes enabling feedlots to avoid over-treating a herd and focusing instead on the calves where more-affordable routine antibiotics are more likely to be effective.

Applicant is thought to have developed a reliable way to quickly, accurately and non-invasively measure core temperature in livestock, by passively detecting the amount of infrared energy coming out from inside the animal's eyes. They have demonstrated that an animal's eye offers great access to the core temperature via the optic artery at the rear of the eye, which connects directly to the core cerebral circulation of the brain. By focusing on the infrared wavelengths that are available from the interior of the eyeball, their technique targets the temperature within the eyeball and near the optic artery, without any significant interference from other sources or from common defects in the eye.

Current technology, using either digital or mercury thermometers, do not provide an accurate indication of core temperature. Rectal thermometer readings are one to three degrees below core temperature This difference is due to fecal material in the colon, lack of contact with the rectum due to gas pockets or simply failing to leave the thermometer in place long enough to get a rectal temperature. At the normal speed of processing, accurate temperature measurements are not made due to time constraints (i.e., 45 seconds using a digital thermometer, 1 minute using a mercury thermometer).

No known accurate, reproducible form of noninvasive measurement of body temperature, specifically core temperature exists. Non core body temperature measurements are less reflective of the body's true temperature. Core temperature is defined as the temperature of the heart and the brain. Currently, the "gold standard" technique to measure core temperature is the invasive placement of a right heart catheter or Swan-Ganz catheter. Current forms of noninvasive temperature measurement include oral, ear (tympanic), forehead (temporal artery sweep), skin temperature, rectal. Only two claim to measure core temperature (tympanic & temporal sweep).

These two forms of temperature measurement have attempted to measure core temperature in a noninvasive form but all have limited accuracy and difficulty obtaining reproducible measurements. These include tympanic or ear thermometers which have difficulty with accurate measurements due to anatomy of the ear canal, excess ear cerumen, excess hair in the canal, and operator error. The other form of measurement is via a swipe over the forehead and the temporal artery area of the forehead. This technique has difficulty with reproducible results and has a high potential for erroneous readings with operator error, sweat, cool skin, etc. Both of these techniques utilize infrared detection technology.

Still other embodiments of the invention relate to products made by the described processes as well as apparatus and systems for performing all or part of such processes. While there are many alternative variations, modifications and substitutions within the scope of the invention, one of ordinary skill in the art should consider the scope of the invention from a review of the claims appended hereto (including any amendments made to those claims in the course of prosecuting this and related applications) as considered in the context of the prior art and the various descriptions of this application.

Many other objects of the present invention will be evident from the remainder of this application in light of a more exhaustive understanding of the numerous difficulties and challenges faced by the prior art, which in turn will be evident to those skilled in the art.

BRIEF DESCRIPTION OF THE SEVERAL VIEWS OF THE DRAWINGS

For a more complete understanding of the present invention and its preferred embodiments, and the advantages thereof, reference is now made to the following descriptions taken in conjunction with the accompanying drawings, in which:

FIG. 10 illustrates the relative depth of emission of various wavelengths from the eye.

FIG. 11 illustrates an alternative embodiment of the invention for microwave and mm wave operation.

FIGS. 13-16 illustrate various embodiments of tags to be used with preferred embodiments of the invention.

DETAILED DESCRIPTION OF ILLUSTRATIVE EMBODIMENTS

Figure 1:
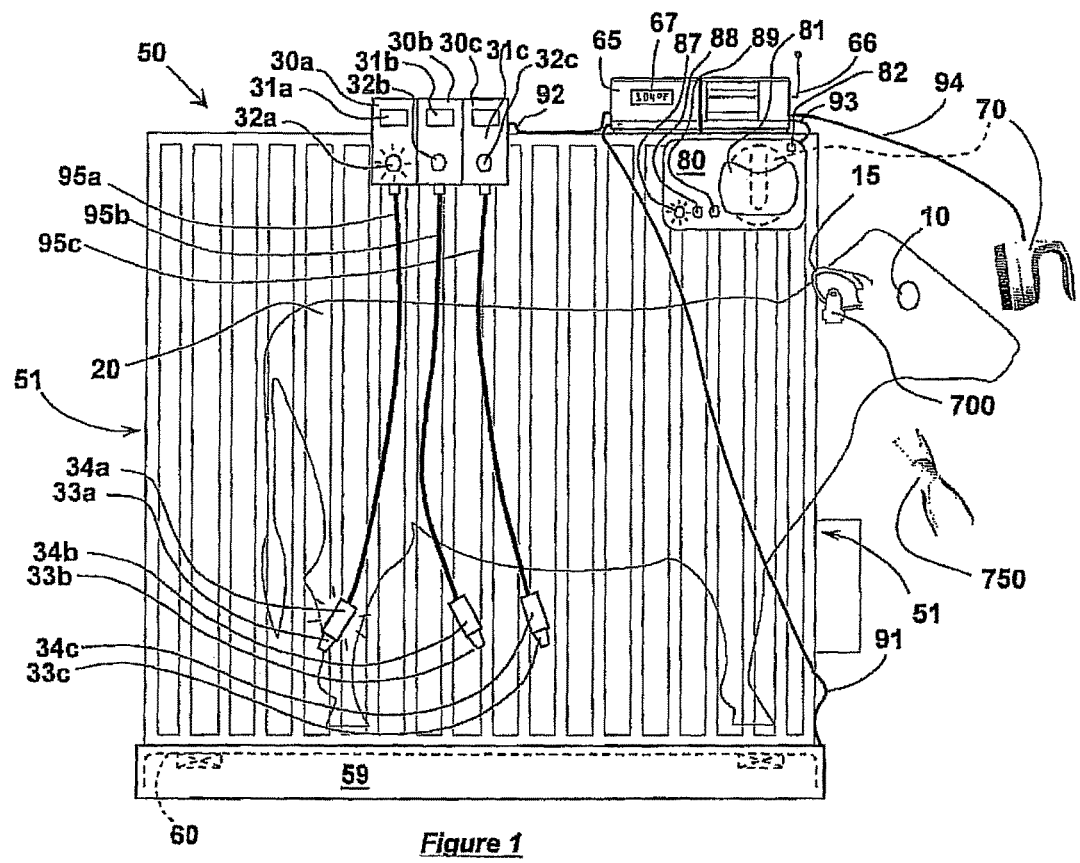
FIG. 1 is an elevation pictorial view of a processing system 11 of certain preferred embodiments.
Figure 5:
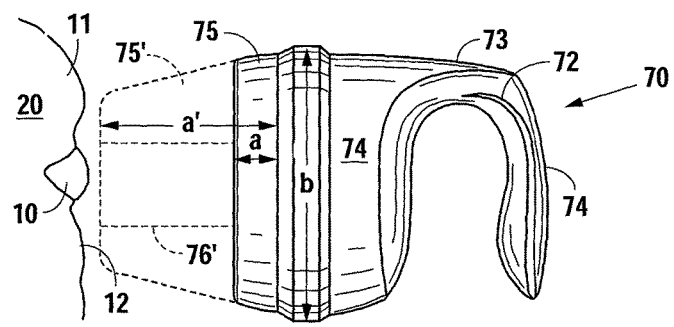
FIG. 5 is a side view of an ocular thermometry instrument according to the teachings of the invention.
Figure 2:
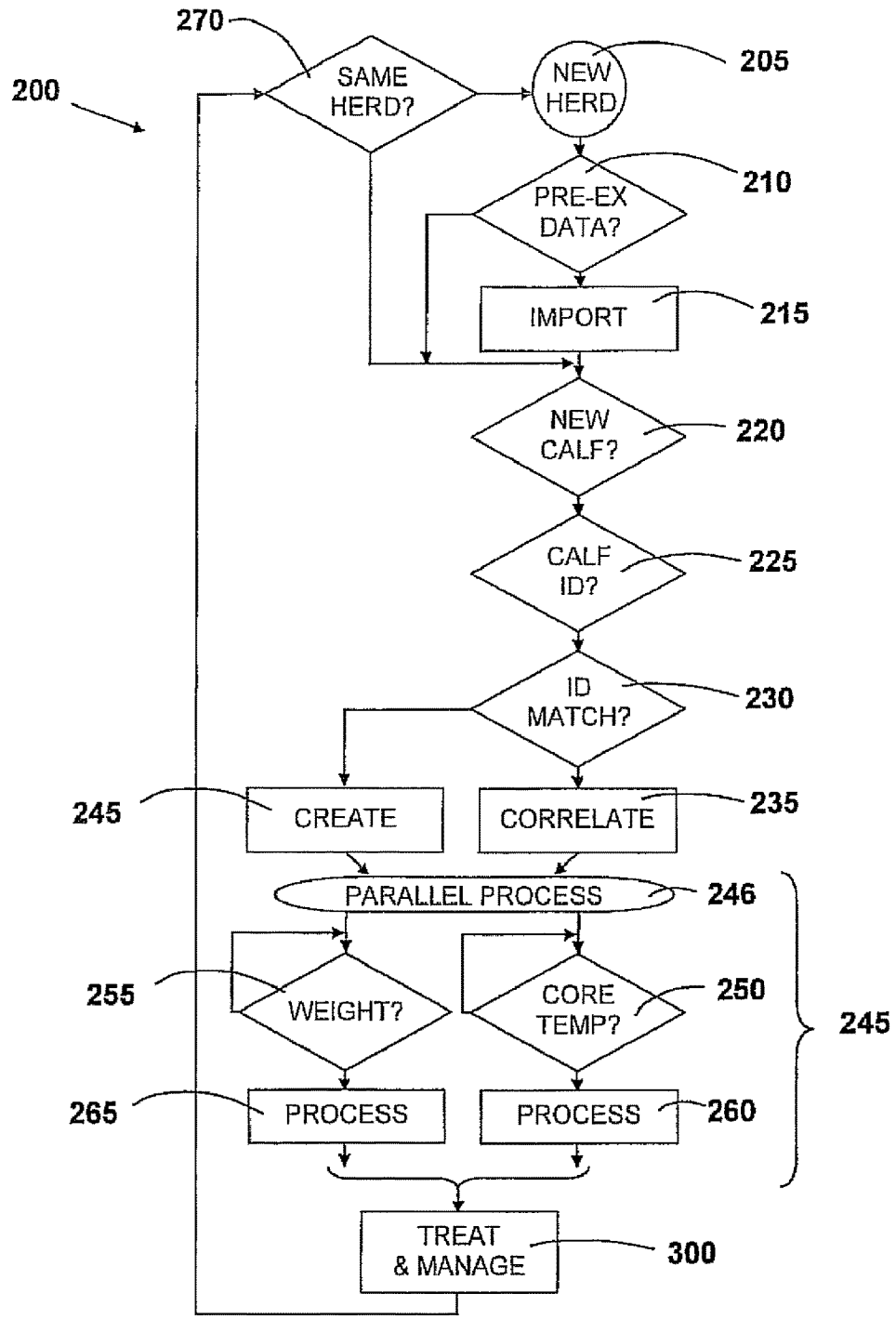
FIG. 2 is a flowchart illustrating a preferred embodiment of a livestock processing method of the invention.
Figure 3:
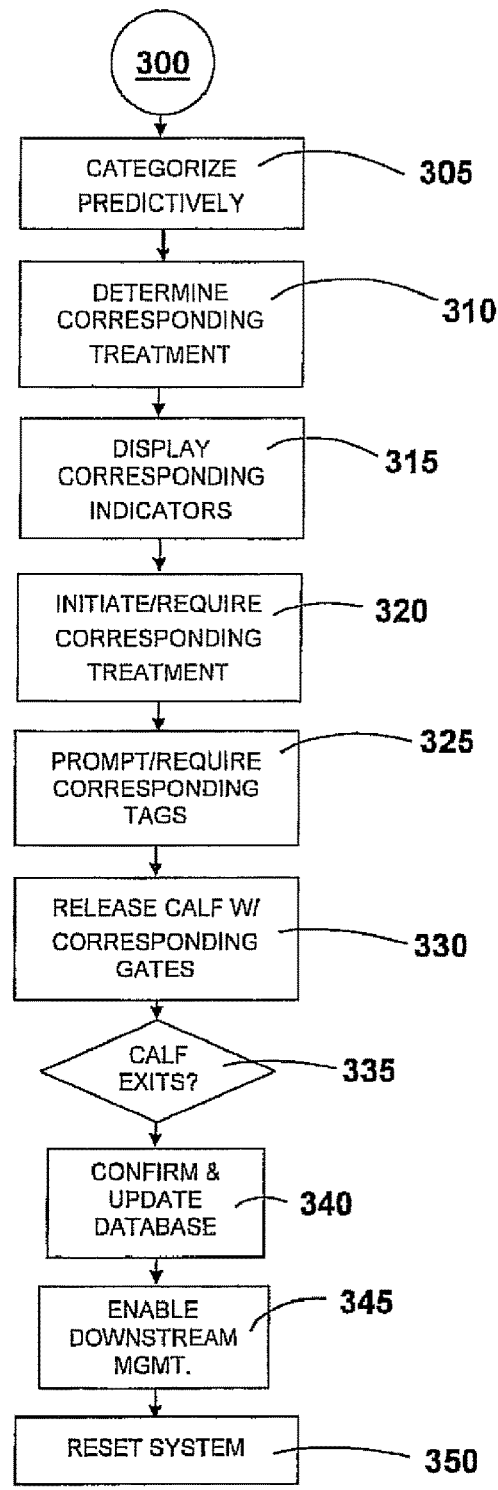
FIG. 3 is a flowchart illustrating preferred detail of the "Treat & Manage Step 100 of the flowchart of FIG. 2.

While our inventions are much more basic than any particular embodiment, one can gather a partial appreciation for some of the possible benefits of the broader inventions and possible interplay between various elements of the inventions in the course of considering presently preferred embodiments. A few embodiments that are presently thought to include the most preferred are depicted in relation to FIGS. 1-16 of the drawings, where similar reference numerals are used for similar elements of various embodiments. The systems and methods depicted therein allow for efficient and effective herd management that draws on reliable yet efficient predictive assessment automatically coupled with corresponding treatment and tagging of the herd, together with related measures for sorting and data management to achieve comprehensive livestock management.

The result yields multiple applications in the feedlot industry, as well as in the dairy and packing industries and in portable systems for use in veterinary applications. As will be evident, some aspects of the invention can even be appreciated in foul or human or other mono-gastric populations. Occasional paragraph or section headings have been used for ease of reference, but such headings generally should not be read as affecting the meaning of the descriptions included in those paragraphs and sections.

Figure 4:
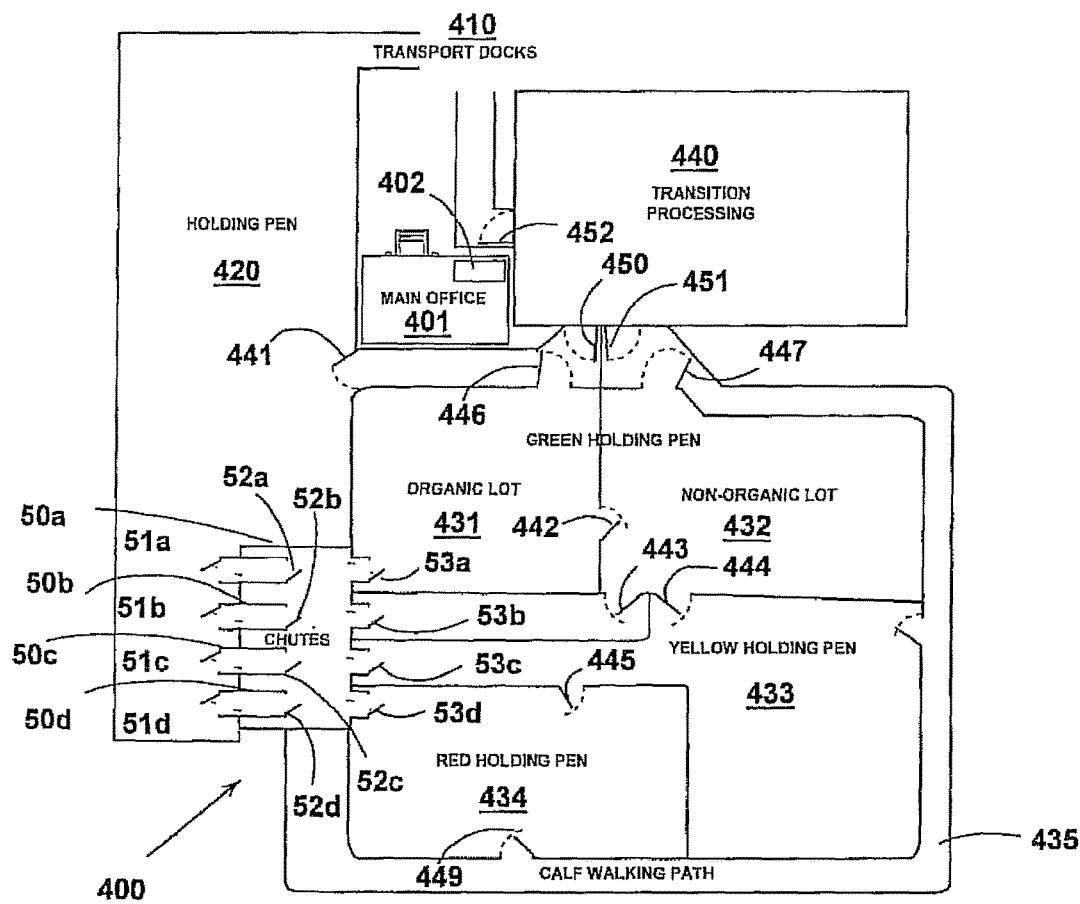
FIG. 4 is a plan view of a cattle feedlot illustrating various embodiments of the preferred methods and systems of the present invention.

CONVENTIONAL HERD MANAGEMENT CONTEXT. Many of the components used in the preferred embodiments of FIGS. 1-16 are typical of conventional feedlots, stockyards and related systems. Although these embodiments are described certain ways that may not be the most ideal for all purposes, those of skill and knowledge in such industries will understand where deviations or substitutions can or should be made from what is described here to make the described embodiments even better or more practical. It will be understood, for instance, that even though feedlot 400 is shown in FIG. 4 with a plurality of pens, corrals, chutes 50*a*-50*d* and gates 51-53 (*a-d* for each) in certain configurations, those of skill and knowledge in the industry will recognize that there are numerous ways of rearranging or adapting the same to make the livestock movement and handling more efficient and practical for feedlot 400. It will also be understood that there are many aspects of such a feedlot 400 that are not shown in FIG. 4 even though they are common if not essential, not the least of which would be feeding and watering troughs as appropriate.

CHUTE MANAGEMENT OVERVIEW. With reference to FIG. 1, there is shown a schematic pictorial view of a livestock processing chute 50 that is representative of any of the processing chutes 50*a*-50*d* in FIG. 4. Chute 50 allows for quick assessment and management of the calf 20 being processed therein. With the features of chute 50 that will be described further herein, feedlot hands are able to quickly (1) administer standard treatments (i.e., any predetermined treatments being administered without regard to the calf's condition); (2) quickly assess the health condition of the calf 20 based on core temperature (in less than five seconds); (3)

administer appropriate treatments in the appropriate amounts to calves in the subclinical and clinical symptom groups; and (4) tag the calf 20 with a color-coded tag corresponding to the grouping of calf 20 based on its assessed condition; all while the calf 20 is in the chute 50. Further, upon release from the chute 50, the calf 20 is then automatically routed to the appropriate pen based on the calf's assessed condition, which facilitates control of various aspects of downstream management of the herd. The result enables not only early intervention for calves that actually need antibiotics or other treatments, but also informed management of the overall herd based on objective standards. More importantly to the management of feedlot 400, the preferred embodiments enable higher quality beef, fewer herd losses, increased feedlot profitability, and potential cost savings.

Other than the special adaptations described herein, chute 50 is preferably a conventional, hydraulically-powered calf chute as is commonly utilized by the feedlot and stockyard industries. In addition to conventional hydraulic positioning arms, upstream gates 51, and downstream gates 52, chute 50 is preferably equipped with an integral scale system 60 for weighing each calf 20 that is in chute 50. Like typical chutes the scale 60 is located at the bottom of the chute 50 and is the platform which the animal stands upon. Also standard of the chute 50 is the lines that are connected to various parts of the chute 50. One of these components is the weight readout 67 which gives the stockyard attendees a visual readout of the weight of calf 20. One of the lines is attached to the scale 60 and then to the weight readout 67. The wire then runs to the top of the chute 50 where a key component of the Herd Management System is located, the CPU 65. Both the CPU 65 and Radio Transmitter 66 are mounted above the chute 50 and are permanent fixtures. While the calf 20 is in the chute 50, as depicted in the figure, a new RFID tag 700 is placed on the ear and the temperature is analyzed with the core temperature sensor 70. Also noted in the figure is the additional need for a remote CPU included in the computer system 402 for feedlot 400 located in its office 401.

When the calves arrive at the stockyard they are placed in a holding pen 420 until their health can be established. In order to accurately establish the health of the calf 20, their health must be verified and they must be given an identification tag. As explained below, the animal should have an identification tag readable visually (such as bar code or simply a number) or readable over a short separation distance by electronic means such as an RFID reader, which may also carry history info on the animal in digital form. This tag may be in place on the animal when it arrives at the chute. If not, one should be added. A temporary color coded tag or attachment to an existing permanent tag may be added to signify the measured core temperature.

The Herd Management System utilizes the latest technology in RFID tagging together with a core temperature sensor 70. The combination of these two elements, the core temperature sensor 70 and the RFID tag 700, create a Herd Management System 11 that has the potential to save time and expense.

CALF PROCESSING FLow. Cross-referencing FIGS. 1-4, upon the arrival of the calves at the stockyard, they are placed in the main holding pen 420. In the past, this is when all of the claves would be inoculated and a brief visual health inspection would be given by those on hand. With the Herd Management System, this is still a necessary step. Once all of the calves have been unloaded from the vehicle dock 410 and placed in the holding pen 420, they are transferred into the chutes 50a-50d for processing and sorting.

CHUTE. By referencing FIG. 1, one can see that the Herd Management System chutes are slightly different that the typical stockyard chute. The Herd Management System utilizes a typical chute 50 with the scale 60 functioning as the floor of the chute 50 and the weight readout 67 on the side of the chute. Also standard are the lines connected to the chute. One of these wires is utilized to send the scale 60 and weight readout 67 information to the central processing unit or CPU 65 that is attached to the top of the chute. Also attached to the top of the chute is a radio transmitter 66 utilized to transmit the data.

Once the calf 20 has been safely secured in the chute 50 the process of health analysis can occur. The heath analysis process should take no more than 45 seconds and in the past this time frame could be challenging, especially if the calf 20 appeared to be ill. In order to properly analyze the calf 20, the weight must be taken and a new identification tag given.

With the new Herd Management System, the temperature can be taken as a necessary part of the health analysis for all of the calves entering the stockyard. The Herd Management System utilizes a new technology, core temperature sensor 70, which allows the core temperature of the calf 20 to be read in a matter of seconds. Once the calf's temperature has been analyzed it is transmitted by radio frequency to a CPU 65 that is installed above the chute. The installed CPU 65 then processes and transmits this data by radio frequency to a remote CPU 402.

The remote CPU 402 processes and stores the data in the central computer system for feedlot 400. The data that is stored in this system is an invaluable resource to both stockyards and ranchers. The data captured by the system can be sorted based upon the needs of the user and is a much quicker and more efficient process. The Herd Management System will help to eliminate some of the inevitable problems that can occur when data is recorded manually.

HERD ASSESSMENT CATEGORIES. Many of the preferred embodiments use noninvasive, relatively-rapid, reasonably-accurate, core temperature assessment as the method quickly and yet reliably assessing the health status of the herd. In addition, however, the same or independent input devices also provide other data to processor 65 for complete tracking and intelligent treatment of the herd of calves 20. Among the data that processor 65 preferably also collects are current ambient temperatures and average daily ambient temperatures, altitude and GPS location data, current ambient humidity and average daily humidity, predicted local bioburdens and weather patterns as provided by veterinarian input or by data from a regional or global database that is networked with processor 65 or the central computer system 402 for the feedlot 400, barcode data or pre-exiting RFID data detected by sensor 70 (with appropriate adaptations), a photographic image of the calf 20.

DRUG IMPLICATIONS. By implementing the diagnostic assessment of temperature sensor 70, one would be able to determine which calves need to be inoculated and which were healthy enough to continue without inoculation. When analyzing the cost and methods of inoculation it is easy to see the benefits of a system that does not require mass inoculation. With common pharmaceutical dosages of approximately 2 cc per 100 pounds the cost can grow rapidly. Most commonly these drugs are injected into the claves with "Felton" injectors; with the cost again rising per injector. Another important factor in cost for inoculations are the drugs utilized. Often, the drugs that are utilized vary in price and brand. Some of the most common drugs utilized in the stockyard industry included: "Biomycin 200" (oxytetracycline), "Baytril 100" (enrofloxacin), "Draxxin" (tulathromycin), and "Banamine/Suppressor". With the general cost of calf inoculation costing $20.00 a head. Mass treatment has become less desirable in the last five years due to increased regulatory scrutiny by the US Federal Drug Administration (FDA), which has virtually outlawed the use of blended cocktail pharmaceuticals. Instead, individual feedlots follow pharmaceutical treatment protocols that vary from region to region and season to season, depending on dominant microbial colonies and weather patterns favoring certain species of bacteria over others. In general, a particular feedlot will follow a treatment protocol that has been recommended by their veterinarian until the feedlot experiences increased disease pathologies within its herds, at which point they will contact their veterinarian for a revised protocol based on regional trends or based on pathogens cultured at the feedlot by their veterinarian, in which case the veterinarian will typically ask the feed lot to retain three deceased animals from the herd, which were not treated with antibiotics For instance, given the wide variety of antimicrobials that are available—e.g., "Biomycin 200" (oxytetracycline), "Micotil 300," (tilmicosin phosphate, which is a deadly cardio-toxin for humans), "Baytril 100" (enrofloxacin), "Draxxin" (tulathromycin), "Naxcel" (ceftiofur sodium)—as well as antipyretics and anti-inflammatories, such as flunixin meglumine (available under the brand names "Banamine" or "Suppressor", in dosages of approximately 2 cc per 100 pound weight, with a cost around $18.00 per 100 cc). Such antimicrobial injectable solutions are typically injected using an injector commercialized under the "Felton" trade name.

In the preferred embodiment, the temperature of the calf is used to categorize the calves of a herd, and the data collected and interpreted by processor 65 allows it to illuminate one of three LED's 87, 88 & 89 colored green, yellow and red, respectively, to communicate to the chute handlers that a tag with the corresponding color should be applied to the calf 20. Tags are applied using handheld tag punch 750 using conventional techniques. Gate interlocks (i.e., automatic gate latches/openers) are also controlled based on this determination such that when the chute processing is complete and the calf is released through the chutes gate 52, the appropriate one of gates 53a-d are simultaneously opened (while the other gates 53a-d are closed and/or latched) such that (a) calves tagged green are automatically routed through gate 53a or 53b to one of two green holding pens (a/k/a "home pens") 431 & 432; (b) calves tagged yellow are automatically routed through gate 53c to the yellow holding pen 433; and (c) calves tagged red are automatically routed through gate 53d to the red holding pen (a/k/a "hospital pen") with the sickest of the cattle requiring veterinary intervention.

Once sorted accordingly, feed lot 400 utilizes a first treatment regimen for calves tagged with a green tag, a second treatment regimen for calves tagged with a yellow tag, and a third distinct regimen for calves tagged with a red tag. For instance, green-tagged calves would generally receive either no treatment or affordable/minimal treatment such as Biomycin. Yellow-tagged calves would receive a slightly more aggressive treatment such as Baytril, which is only indicated for bovine respiratory disease, (BRD) associated with certain microbial species. Red-tagged calves would receive even more aggressive treatment such as the combination of Draxxin together with Banamine, as well as direct oversight by a veterinarian.

To further automate this treatment, processor 65 uses the green, yellow, red determination, together with data collected and interpreted by scale 60, to automatically set the dosing of medical treatments to be administered to the calf 20 by treatment pumps 30a-30c, where pumps 30a, 30b & 30c contain the treatments for calves in the green, yellow and red groupings, respectively. Although shown schematically in FIG. 1, it should be understood that treatment nozzles 33a-33c are whatever type of medicine-delivering equipment is appropriate for the corresponding med, whether the equipment be an injector or a sinus sprayer or whatever else may be desired for the meds being used. Additional illuminators 32a-c and 34a-c are illuminated to convey to the calf handlers the particular pumps or nozzles, respectively that should be used for the calf 20, as determined by processor 65 based on the calf's temperature as assessed by the temperature assessment system 70.

COLOR-CODED TAGGING SYSTEMS. To facilitate the sorting and management of the herd after the calves are out of the chute, preferred embodiments use color-coded RFID tags 700 for quick, visible recognition of the calf's condition and/or recent treatment history. In a presently preferred embodiment, three colors are used: green, yellow, and red. The color of tag used for a particular calf 20 depends on which of three populations the calf 20 falls into at the time: the asymptomatic group (below 104 F—tagged as green), the subclinical group (104-105 F—tagged as yellow), or the clinical group (above 105 F—tagged as red) that typically require multiple treatment days.

Later, after processing through chute 50, when a handler or veterinarian reassesses the calf 20 at a later point in time, the non-RFID color tags would be made available as accessory markers to be used on the animals where visual tracking and sorting is needed. This would also be used in selected fields by the rancher or dairy farmer as a visual ID on the animal when utilizing the device as an everyday core temperature tool.

Once the calf 20 has been analyzed and an assessment of health has been made, the calf 20 must then be tagged based upon this heath assessment. Prior to this the old tag must be removed from the calf 20 and a new RFID tag 700 attached. The Herd Management System utilizes a color coded RFID tagging system based upon the health of the calf 20. A calf with a core temperature of less than 104° F. is tagged with a green RFID tag 700 and is not inoculated due to its health status. A calf with a temperature of 104° F. to 106° F. should be tagged with a yellow RFID tag 700, inoculated and have its health monitored. A calf with a temperature greater than 106° F. should be tagged with a red RFID tag 700, inoculated and a certified veterinarian should be contacted to further analyze the calf's health needs.

The RFID tags 700 have a multitude of options to suit the stockyards needs. The tags can be utilized in one of two ways. The data that is stored and transmitted through the radio frequency transmitter 66 to the associated CPUs 65, 402 can display only the tag number which can then correlate to the associated data. Another option is for the RFID tag 700 to actually contain the data of the specific calf 20. Either option will utilize the benefits of the Herd Management System and ease the burden of the stockyard attendees.

TAGS. FIGS. 13-16 depict the RFID tagging options that are currently preferred embodiments, each having different levels of benefits and deficiencies. FIGS. 13-16 illustrate four of the alternative embodiments for tags 700, although others will also be evident to those of skill in the art. Tag 700a consists of a black button 701 in the center of a colored disk 702. Tag 700b utilizes the same size tag with the black button 701 center; however, the associated disk is neutral. The RFID tag 700b is then encompassed by a colored jacket 703 showing the calves status. The alternative embodiment as tag 700c utilize the same RFID tag but in different ways. Both RFID tagging options contain a neutral disk 702 with a black button 701 center. Above the black button 701 center are three colored punch buttons 705-707 that correspond to the Green, Yellow, and Red tagging system. These buttons can be left intact or punched out depending on the needs of usage for the stockyard. The final illustrated alternative embodiment of tag 700 is tag 700d, is the largest of the tags. It utilizes the same colored disk 702 and black button 701 center as Tag 700a. This RFID tag, however, has an additional hanging tag attachment 710 attached to the main colored disk 702. Within this hanging tag 710 the calf's identification number 711 is displayed.

TAG VARIATIONS. The RFID tags 700 also have a number of alternative embodiments with sizes and characters of the tags 700. Several of such alternative embodiments 700a-700d can be seen in FIGS. 13-16, respectively. The first of such variations is represented in tag 700a, which is the most simplistic of the illustrated embodiments. It consists of a round RFID tag 700a with a black button center 701 and an associated color coded disk 702 surrounding it. Tag 700b is similar in size and shape to Tag 700a. However, 700b has a colored jacket 703 that is pinned to the RFID tag 700. The embodiment 700c of tag 700 utilizes the same basic construction with disk 702, except that group identifying information is visibly conveyed with RFID tag 700c through the use of punch-outs 705-707, which are colored green, yellow and red, respectively. The differences are the colored punch buttons 705-707 located at the top of the neutral colored RFID tags 700. These buttons can be punched out according to the health of the calf 20. Embodiment 700c of tag 700 allows the wrong colors to be punched out, allowing only the correct health status to be shown. Alternatively, the inverse of tag 700c allows for the correct health status to be punched out and the remaining colored punch buttons to stay intact. The final and largest of the colored RFID tags 700, namely tag embodiment 700d, includes a combination of Tag 700a and a larger tag attachment. The larger hanging tag attachment 710 will connect to the RFID tag 700d and add a visual identification number 711 and/or a bar-code (not shown) to the RFID tagging system.

Embodiments of the present invention combine tags with methods to help track health information as well as origin and other information. Further particulars of each of such RFID tags 700 will be evident to those of ordinary skill in the livestock tagging industry and/or the RFID industry. The most common RFID tags 700 currently on the market are manufactured by "Allflex." TekVet also currently has a temperature sensing module that is attached to the ear.

As stated above, the animal may be already tagged with an electronically readable (such as RFID) tag upon entry into the chute. If not, it is tagged with such a tag. The additional color-coded "tagging" may be a second tag, or an addition to an existing RFID tag, with the color of the second tag or the additional tag representing a range of core temperatures. The color-coded core temperature tag need not be a permanent tag, and may be a temporary attachment to an existing tag or a temporary tag (collectively referred to herein as a "tag").

SORTED PENS/CORRALS. Once all the calves have been processed thru the chutes 50a-50d they are then be sorted into their appropriate holding pens 430-434.

FIG. 4 depicts the layout of a general stockyard utilizing the Herd Management System. The process begins with the claves being unloaded from the vehicle dock 410 and entering the holding pen 420. From there the calves enter the chutes 50a-50d and are analyzed according to the Herd Management System protocol. Once the calves have been analyzed they are distributed to their appropriate holding pens 430-434. Each holding pen has 430-434 an associated color depending on the health status and feeding guidelines of each calf 20. All holding pens 430-434 have the ability to utilize the walking path 435 to re-organize or re-evaluate calves. Also located on the stockyard grounds is the slaughter facility 440 where the calves are processed once their ideal health and weight have been achieved.

The Herd Management System relies on these standard methods but can alleviate much of the cost associated with large herds. The process for corralling and handling the calves is in many ways the same but there are several key differences. The process of the Herd Management System and an explanation of components can be found in the remaining paragraphs.

GATE INTERLOCKS. Once the calves have had their health analyzed and new RFID tags 700 attached they are released into their associated holding pens. A stockyard typically has several pens for holding and feeding regimens depending on the calf's health. When utilizing the Herd Management System, this process is made simpler by having the calves easily identifiable. In figure B, one can see that once the calves leave the chutes 50a-50d they are sorted into the above mentioned holding pens. In the diagram you can see that there are three main holding pens. A red holding pen 434, for those calves that have been given a red RFID tag 700 and are need of medical care. There is also a yellow holding pen 433, for those calves that need to be monitored and were tagged with a yellow RFID tag 700. A green holding pen 430 is utilized for calves who have been determined to be in good health and have received a green RFID tag 700.

DOWNSTREAM. In many applications, once a herd is received from a certain source (i.e., certain rancher), and processed into the feed lot, a pen rider will visually observe the herd in the proceeding time period, watching for signs of sickness or disease . . . often manifested by droopy ears, visible congestion, loss of weight, or death. When a sick calf is then identified within the herd, the pen rider can then make quick conclusions about the calves prior treatment and possible future treatments based from the colored tags on the calves ear.

ORGANIC SUBHERD. The green holding pen 430 can be further divided into two sections, an organic 431 and non-organic lot 432. By tracking the calf's data electronically a stockyard would have a better ability in keeping the associated calves separate and in better health. All associated holding pens 430-434 would have different feed and treatment regimens as necessary. Additionally, the entire associated stockyard holding pens 430-434 would have the ability to use a calf walking path 435. This path gives the stockyard attendees the ability to transfer calves from one holding pen to another or to re-evaluate them in the chutes 50a 50d. Once the calves have reached their ideal weight and health they can then be transferred from the stockyard to the transition facility 440, which may itself be a slaughter facility or a staging area for shipment to slaughter or another desired location.

The Herd Management System utilizes advanced technology to ensure that the standards of the Department of Agriculture and the Food and Drug Administration are upheld. By employing a Herd Management System like this a stockyard could see and increased profit margin and a higher standard of quality. By not inoculating all calves that enter the stockyard, there is a potential for greater and more rapid weight gain. This type of Herd Management System also allows for the ability to ensure that those with an organic potential are clearly identified.

PORTABLE ASSESSMENT. The Herd Management System also utilizes a portable hand-held reading device that can be used in conjunction with the overall system 50. Much like the core temperature sensor 70, the portable reader can be used by pen riders or veterinarians as a portable data collection device to be used either in the pens 420-435 or at other remote locations. The portable reader is an alternative embodiment of sensor 70 that is battery powered and can be carried on horseback or by hand wherever an assessment needs to be made. The portable reader preferably has all the functionality of sensor 70, together with a digital display for use by veterinarians. This portable reader would be ideal for veterinarians needing to analyze calves in and out of the stockyard environment. As with the larger system, the data from the core temperature sensor 70 would be stored within an electronic database, which is customizable based on the needs of the user. Preferably, the portable reader has its own memory while also interfacing wirelessly with the database 402 in the central office 101. The Core Temperature System 70 is a minimally invasive device with accurate results. The use of a core temperature sensor 70 can help to reduce veterinarian bills for services rendered and through medication needed.

Data Management System.

SOFTWARE. The subsystems that are used in the system may be licensed parts and software programs that have been custom developed or modified by existing manufacturers currently in the ID field. Another element that advances the Herd Management System beyond the prior art is its ability to minimize the amount of time required to analyze and document a calf's health needs in preparation for slaughter.

Preferred embodiments also include a networked data processing system. This system is adapted and used to access, analyze, or manipulate any of the data captured by the Core Temperature System 70 or the RFID tags 700.

Overall, the Core Temperature System will be a great asset to the stockyard industry. It has great potential to improve standards and reduce overall costs. Initially, these savings will be of a greater value to the stockyard and the benefits will be passed on the consumer. By utilizing a core temperature sensor 70 a stockyard has the potential to ensure that only the healthiest and strongest of calves get processed. By ensuring such standards, the stockyard can ensure customers their product is not only free of disease but the overall quality of the meat is and will continue to be exceptional.

INDUSTRY-WIDE DATABASE. Many other features and alternatives also fall within the scope of the present inventions. One particular alternative embodiment adds another level of data collection and management that collects "de-identified" data from the entire customer base of users of system 11 in order to develop a near-industry-wide database that correlates livestock conditions and outcomes. When the system 11 is installed at the feedlot 400, the owner of the feedlot 400 consents to the collection of such de-identified data, and a protocol is integrated into the computer system 402 for periodically downloading the de-identified data to a global clearinghouse where the data is further processed to develop predictive algorithms to aid in management of livestock by subsequent users.

One particular variation of such portable reader utilizes the AT&T cellular phone network and the Apple I-Phone platform in the data collection and data download function. This variation preferably collects and assimilates non-temperature data about an animal through the conventional input systems of the Iphone platform and collects temperature data through a temperature data collection module. The non-temperature data collection preferably includes data in three forms: a picture of the animal, a picture of any identifiers on the animal (such as brands, tag numbers or barcodes), and audio and text data about the animal, to include general commentary as well as specific data about the condition of the animal and any treatment being administered. The temperature data collection module is in the form of either a connected portable reader (i.e., a portable reader as described above, that is data connected to the I-Phone platform), or through an upgraded hardware system of the I-phone platform. The upgraded I-Phone hardware system preferably includes an infrared image collector that either replaces or augments the visible light camera of the I-phone platform. Hence, the upgraded I-Phone platform is able to collect both visible and infrared images.

Although all processing could be conducted in the computer system 402 of the office 401, or in another computer system connected with the global database, the I-phone platform is also preferably adapted with local software Apps that process the collected data before sending it to the centralized system 402 or the global database. Such Apps preferably include software modules for: (a) converting the infrared image(s) to an indicator of the core temperature of the animal (in accordance with other teachings of this invention), (b) converting images of animal's identifiers into more specific (e.g., converting an image of a numbered ear tag into the actual number printed on the tag and converting a barcode image into an actual barcode number), (c) converting text images into text, and (d) translating audio files into text. Once the data is collected and processed on the IPhone platform, this portable variation is further adapted and used to download all or part of the data through the AT&T cellular network to the computer system 402 for local data management at the feedlot 400, while de-identified data is downloaded to the global database where the de-identified data is compared to pertinent database of conditions, outcomes and recommendations, and the global database transmits corresponding likely outcomes and recommendations through the cellular network back to the I-phone so that the user can make more intelligent decisions in treating the animal.

BUSINESS METHODS. The costs of managing a herd can be alleviated in some ways due to the leasing options available with the Herd Management System. By utilizing the various embodiments of the invention, herd managers are able to predictively sort a herd for management purposes. The rapid core temperature device and the subsequent ID system products can also be implemented in a business method to make this unique tracking package easier for the end user to acquire as a leased product in the market. This lease would allow the product to move more quickly throughout the industry because the operating costs for the end user would be lower and easier to justify. Moreover, with such enhanced management, users of the product can enjoy savings on medications, higher market price for the resulting product, grants, etc. Distribution of system 11 and associated software may utilize the logistic support of established channels already in the markets. Alternatively, parts of the application will be split by regions, territories and in-house channels.

Core Temperature Assessment.

To serve as the core temperature system 70 component of the overall systems and methods described herein, FIGS. 6-12 show various embodiments of a core temperature assessment system usable in the herd management systems of FIGS. 1-5. The core temperature assessment system of FIGS. 6-12 provides rapid and accurate non-contact measurement of electromagnetic thermal emission and relates such measurements to the core temperature of the animal or person. Core temperature is the actual temperature of the animal's vital organs. Currently, the only accepted way to actually measure core temperature is with a thermister equipped Swan-Ganz catheter inserted into the heart via jugular veinapuncture. Applicant's technology non-invasively measures core temperature from the anterior chamber of the eye—no incision, no vein puncture, no sutures, no risk of complications or infection. It overcomes the limitations of previous thermal emission thermometers by non-contact sensing of thermal emissions only from the eye of the subject. The eye provides a target with many desirable properties for such measurements. It is readily accessible, generally very clean, has a high emissivity, is quite uniform from one person or animal of the same species to another, and is continuously bathed with fresh body fluids, internally and externally that maintain the eye near the core temperature. The wavelength of eye emissions that are sensed for such temperature measurements may be of microwave, millimeter wave, or specific spectral bands of IR wavelengths. It may also be a combination of more than one wavelength or spectral bands within these ranges, optimized to be most suitable for the intended application.

Criteria for optimization of the detected wavelength include: (1) suitability for non-contact sensing of the emission from a spot the size of the eye or smaller, or a selected portion thereof, while minimizing the sensitivity to emissions from regions outside the said spot; (2) maximizing the depth into the eye from which emissions are detected to insure the highest correlation with core temperature, while maintaining an acceptable instrument sensitivity measurement error; (3) freedom from effects of the environment, natural and manmade, on the measurement; and (4) measurement time for sufficient accuracy.

The method uses electromagnetic (black body) emission from the eye of the animal or person to accurately and rapidly assess temperature. This hands-off method is effective and efficient in the early detection of disease. This facilitates the rapid use of proper treatment regiments and reduces the overuse of antibiotics and thus the antibiotic residue in meat and milk supplies.

In the example of this description, the method obtains accurate core temperature indications by using the measured thermal electromagnetic emissions, from the eye of the person or animal, that are within one or more spectral bands centered at specific wavelengths and of specific bandwidths. The eye is accessible from outside the animal and has the possibility of providing an accurate core temperature indication—especially if emission from within the eyeball is utilized.

Figure 6:
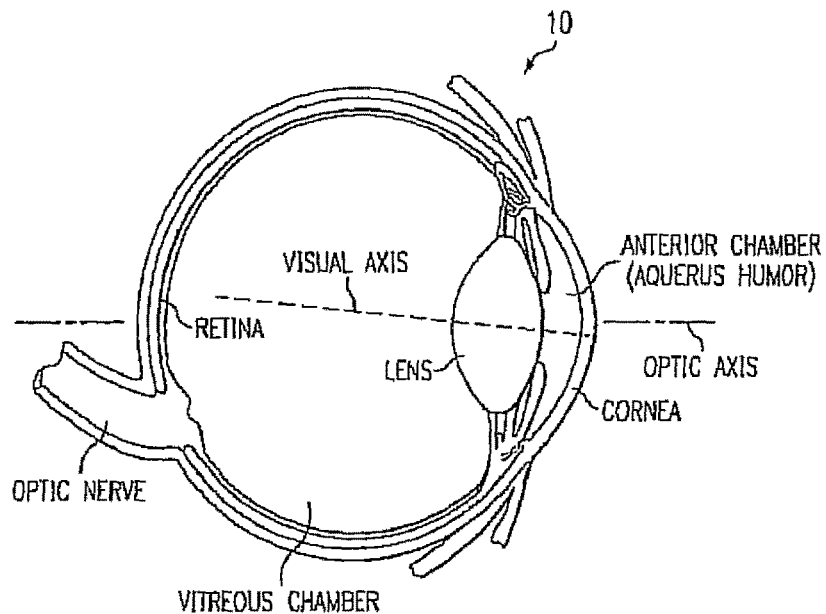
FIG. 6 is a cross sectional view of the eye of a mammal, such as a cow.

FIG. 6 is a cross sectional view of the eye of a mammal, such as a human or animal. The eyeball is continuously bathed by body fluids, and has continuous blood flow within the exterior wall and in the eye socket and eyelid regions. These tend to keep the eye interior temperature very near the body core temperature and to keep the external surface relatively clean.

It is known from laser safety guidelines that only visible and near-infrared (400-1400 nm) wavelengths of electromagnetic radiation (light) can readily penetrate the aqueous, cornea, iris, lens, and vitreous and be focused on the retina at the back interior of the eyeball. Similarly, emissions from these interior regions will pass through the front of the eye and may be detectable externally by use of a suitable sensor should such a detector exist but unfortunately now does not. Mid-infrared (1400-3000 nm) and far infrared (3000 nm to 1 mm) are absorbed in the front surface of the eye, though some mid-infrared (sometimes called short wave IR) of (1.4-2.5 microns) penetrates deeper through the cornea and through the sclera. Far infrared thermometers primarily detect emissions from the exposed outer surface of the eye—due to high absorption of such wavelengths of infrared emissions coming from the interior by the vitreous, the sclera and the near surface layers of the eyeball. While these emissions could be near the core temperature, the eye surface emissions will be much stronger, but are not of the eye temperature. In addition, the eye surface may not always be sufficiently insulated from the effects of tear evaporation, environmental temperatures, wind, rain, etc., to provide an accurate correlation with core temperature. Emissions from the lens, vitreous, and retina interior, which are deeper within the eyeball, meet the criteria for more accurate correlation with the core temperature. Sensing of the specific bands of emissions from the interior regions of the eye provides a useful basis for obtaining accurate core temperature with a non-contacting sensor.

Figure 7:
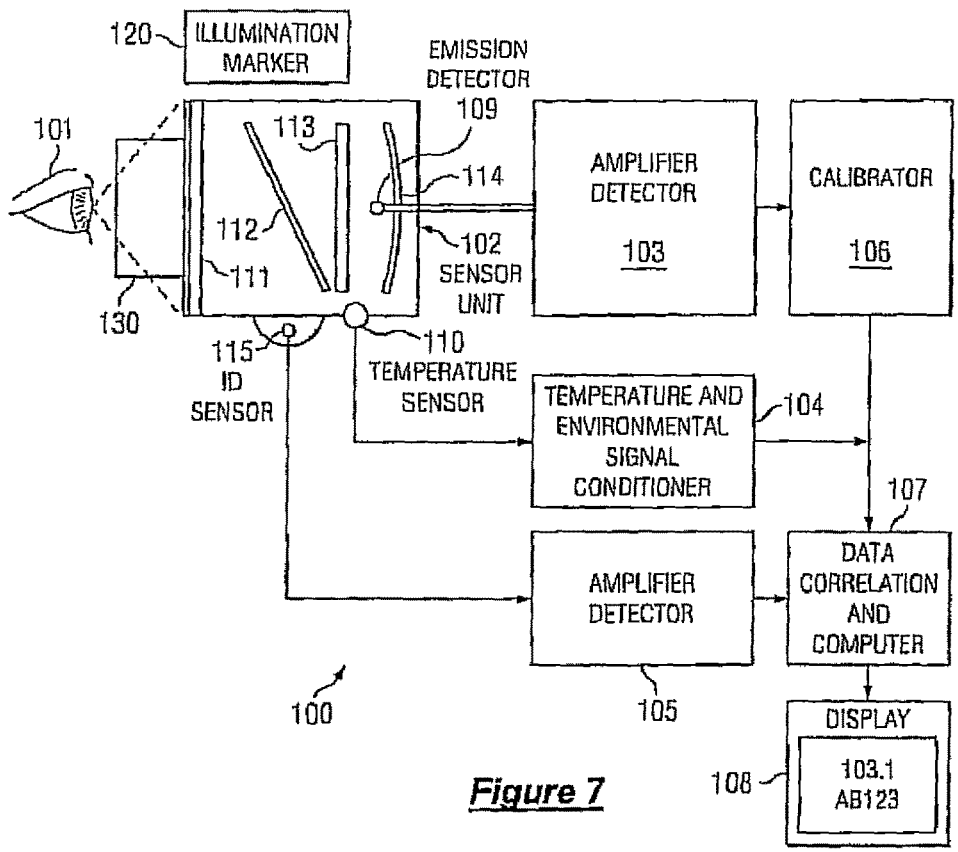
FIG. 7 is a block diagram of a first embodiment of an ocular thermometry instrument of the invention.

FIG. 7 illustrates a core temperature measurement device 100 in accordance with the invention. A sensor unit 102 contains the detector 109 and auxiliary apparatus needed to sense the thermal (Planck) emission of selected wavelengths from the eye 101 of an animal or human. The sensor unit 102 also contains various optics elements, such as lenses, a mirror, and filters for focusing the emission of interest on the detector 109 and filtering the emission to allow only wavelengths of interest to reach the detector 109. It may also contain a means to reduce the temperature of the detector 109 to increase the sensitivity of said detector and it may also cool optical lens and filters to reduce thermal emissions from all components which would be seen by the detector 109. In the example of FIG. 7, sensor unit 102 contains an IR filter 111, a half mirror 112, a spectral filter 113, and a parabolic reflector 114. A light shield 130, for example, a rubber eyepiece, may be used to minimize non-related thermal emissions during the measurement and to set the separation distance from the eye to the sensor unit.

In the example of FIG. 7, sensor unit 102 detects IR emission of the spectral wavelength bands of interest. The optical components provide a sensitive aperture for detection of eye emissions passing through this defined region of the eye surface. The area of this aperture 10 may be near the area of the eye or a selected portion thereof. The sensor unit 102 provides such an aperture at a distance of a fraction of an inch to a few inches or more from the front of the unit.

The sensor unit 102 also contains auxiliary sensors for sensing the temperatures of the assembly and other environmental parameters needed to compensate for their effects on the core temperature measurement. In the example of FIG. 7, a temperature sensor 110 obtains a temperature measurement. An identification (ID) sensor 115 senses data needed to identify the particular animal or person being measured. For example, ID sensor 115 could be used to read a bar coded tag on the animal, it could be a radio frequency Identifier (RFID) or it could sense unique optical characteristics of the eye. The optional filter 111 allows a broad wavelength band of emission of interest to pass to the detector 109 but rejects emissions outside this range. The broad wavelength bands of interest include those used for eye temperature measurement and those used for animal identification and may also include those used for producing a visible spot or direct optical viewing for properly aiming the sensor 102 toward the eye to be measured. It also acts as a dust and water seal to protect the interior of 102 from the environment. Filter 113 passes wavelengths needed for the temperature sensing. Means to use multiple filters of different wavelength bands are also a part of the invention.

Rather than use the plastic cover, a disposable eye cup or thin plastic film on the end of the lens piece can be used as alternatives. This is very much like the disposable piece that goes on the end of an otoscope (instrument an MD uses to look in your ear).

Illumination marker 120 provides a visual indication of the region of the eye 101 that is being examined for core temperature measurement. In other words, marker 120 provides a spot of visible light on the eye that corresponds to the aperture area of sensor unit 102. For example, marker 120 might provide a spot of light on the eye when the detector unit 102 is properly aimed toward the eye. The marker 120 permits the operator to stand away from the animal and know that sensor unit 102 is aimed towards the desired eye region. The spot of light serves the additional function of attracting the animal's attention and thereby facilitating measurement.

The output signal from the emissions detector 109 goes to the amplifier-detector 103 which boosts the amplitude of the signal and detects the amplitude of the emissions from the eye. The detected signal is normalized and calibrated in terms of the temperature of the emitter by the calibrator 106. The eye emission data from measurements of live humans and animals is initially calibrated to a precise surgically invasive core temperature thermometer such as the Swan-Ganz Catheter or Pulmonary Artery Catheter. During such initial tests the animal (calf or other) is restrained under veterinarian care to minimize movement and allow access for an adequate series of measurements to be made. Vaccines, such as pasturella, provide a harmless means for temporarily raising the temperature of test cattle by up to about five degrees above the normal range of 100-103 F. to provide a range of core temperatures for as needed for calibration.

Initial calibration data for human core temperature will be obtained using a surgically invasive thermister probe such as the Swan-Ganz for comparison with the eye thermometer measurements under medically suitable conditions as available.

The output of the temperature sensor 110 (and any other environmental sensors) is connected to the temperature and environmental signal conditioner and control unit 104, where the signal is amplified, normalized and used to provide correction data needed to compensate for and improve the accuracy of relating the emissions data to the core temperature of the animal or human. For example, changes in temperature of the sensor and associated components can affect the detector sensitivity and "zero signal" output level as well as the magnitude of nonrelated thermal emissions that reach the detector. Corrections and compensations that are needed are performed by the data correlator and computer 107. If desired, conditioner and control unit 104 may include means for maintaining sensor unit 102 at a constant temperature. It may also be cooled to improve sensitivity by use of a thermoelectric cooler or cryogenic fluid in an insulated enclosure about the detector.

Identification sensor 115, through amplifier-detector 105 also provides data to the data correlator and computer 107, which provides a visual, numerical readout of the core temperature, identification data, time, date, environmental temperature, and other pertinent information on display 108. The core temperature is computed from the amplitude of the eye emissions, of a selected wavelength and spectral bandwidth, corrected for effects, if any, of environmental and instrument temperature, distance from the eye to the sensor assembly 102, region of the eye that is measured and the type of animal as well as for instrumentation variables of amplifier gain, detector gain and sensitivity, and pre-detection bandwidth. This readout data is also stored in the computer 107 for later recovery or for transfer to an external data storage facility for long time retention. Display 108 may also display other information, such as an animal's rectal temperature, breed and other identifiers. Corrections for instrumentation effects are stored in the instrument computer and periodically updated between quality checks to facilitate accuracy.

FIG. 10 illustrates the infrared and visible light transmission properties of the various regions of an eye 10. As illustrated, the visible and near-infrared (400-1400 nm) wavelengths of light are transmitted with small attenuation through the cornea, aqueous, iris, lens and vitreous and focused on the retina at the back of the eyeball. Longer wavelength light in the mid-infrared and far-infrared (wavelength range of 1400 nm to 1.0 mm) are, except for a few discrete bands of wavelengths, greatly attenuated in the cornea but some mid-IR wavelengths (near 1600-1800 nm and 2150-2350 nm), may penetrate an appreciable distance into the eye interior or be received externally as IR emissions from the eye interior—these are used by the instrument to obtain core temperature data. Similarly, thermal emissions will be transmitted from the retinavitreous region through the lens, cornea, aqueous, and iris to the outside in corresponding wavelengths of low attenuation. Mid-IR at wavelengths 1000-2400 nm may also be transmitted through the sclera which covers the entire eyeball except for that covered by the cornea. Thus, far-infrared emissions from the eye will be primarily from the surface, whereas the weaker mid- and near infrared emissions, especially of certain bands of wavelengths, will penetrate the front part of the eye and be more representative of the interior eye temperature. Millimeter waves and longer wavelengths of emission will be representative of temperatures deeper within the eye interior than those of the far infrared wavelengths. IR detectors operating at far infrared wavelengths may be used to sense emissions from the tear duct area of the eye that also correlate to lower accuracy with core temperature.

To obtain electromagnetic emission data from deeper into the eye, the use of shorter IR (0.8 to 3 micron) wavelength ranges is advantageous. The wavelength range that is sensed is set by the type of detector 109 and by the use of filters, such as filter 111, ahead of the detector to restrict the range of emission wavelengths that fall upon the detector. For wavelengths greater than about 1.5 microns a broadband thermopile detector or some photodiodes, such as cooled extended range indium arsenide or extended range Indium Gallium Arsenide photodiodes, cooled or at ambient temperature, provide good sensitivity and are commonly used either with or without IR filters to restrict the bandwidth of the detected emission. For shorter wavelengths, other photodiodes (germanium, silicon, gallium arsenide, and several others) with various dopants or photomultiplier type sensors provide good sensitivity, either cooled or not cooled. IR bandpass filters are used to restrict the wavelength range of the emissions that are detected. Otherwise the emissions from several regions of the eye would be detected simultaneously. The surface emissions, representing the surface temperature of the eye, can be much larger than those from deeper into the eyeball. Unless corrected for wavelength (or otherwise) these surface emissions will cause errors in measuring the desired (internal) emissions that, in most cases, will be most representative of the core temperature. A far-IR detector will respond entirely to the surface temperature, which in general, is much more susceptible to environmental effects than are the internal emissions. Conversely, the low attenuation in the eyeball at visual and near-IR wavelengths would be most suitable for transmitting emissions from deep into the eye back to the retina region. This is desirable since the retina region is best isolated from environmental effects and the temperature is best correlated with core temperature. Unfortunately, there is a problem with the intensity of the Planck emission at these short (visual and near infrared) wavelengths. In practice the emission from a black body at live animal temperatures (300-310 K) is so weak that it is undetectable at visual and at the shorter near IR wavelengths even with the best detectors. Even at 1000 nm, the emission at these temperatures, from a target at about 30 d K, is still so weak that it is not rapidly detectable. The instrumentation question then becomes, for a small, hand held thermal emissions detector are there any IR wavelengths where internal eyeball temperatures are accurately measurable (to 0.1 K) in an acceptably short time (few seconds), from a stand off distance (range) of a few inches? The answer is yes if an extended (wavelength) range indium gallium arsenide detector, or an equivalent, is used at wavelengths in the 1600-2400 nm range, particularly in either or both of the two bands, 1600-1800 and 2150-2350 nm that provide the lowest attenuation for internal eye emissions as was previously mentioned. A preferred embodiment of the invention uses a said type extended range InGaAs detector with optical filters that will pass emissions of nominal wavelengths 1600-1800 or 2150-2350 nm, or both, along with collecting and focusing optics that will create an IR sensing region (of a size equivalent to the cornea or larger) when the detector 102 is at a selected distance, for example 0.5 inch to several inches from the eye to be measured.

Another detail of the invention addresses additional means that are utilized to further reduce the effects of emissions coming from different depths in the eye or from extraneous, non-related sources and to thereby improve the measurement accuracy. The desired thermal emissions that best correlate with the core temperature come from the interior of the eye. However, other (unwanted) thermal emissions will be detected from the surface and near-surface of the eye. These may be at the same temperature as the desired interior emissions, at a higher temperature or at a lower temperature. In any case the surface and near-surface emissions can be expected to vary a small amount with changing environmental temperature, wind and rain and thereby cause measurement errors. The interior emissions will only be of appreciable intensity at the wavelengths where the eye attenuation is minimal (these are the same wavelengths as the optimum detector filter(s) while the surface and near-surface emissions have a much wider spectrum with intensity drastically increasing at longer wavelengths. By comparing the total emission detected through the said narrow band filter with the total emission detected with a wider band filter, or with a filter of different center wavelength, the component due to internal emission will not change (except for different attenuations in the band filter) while the detected surface emissions will increase significantly with a broad filter. By knowing the spectral band pass characteristics of the broad filter and of the detector, the emissions from the eye surface and spurious sources are determined and a correction factor is derived for the interior eye temperature measurement.

FIG. 11 illustrates a microwave and millimeter wavelength, or terahertz (THz), detector 40, which is an alternative embodiment to the sensor unit 102 of FIG. 7. Another possibility, within the scope of the invention, for obtaining eyeball interior temperature data is to detect emission in the longer wavelength (compared to IR) microwave and millimeter (mm) range. Sensitive detectors, using normal radio frequency superhetrodyne (mixer-oscillator) techniques, are available at modest costs for the nominal 3 mm (80-100 GHz) range as a result of commercial and government interest in this part of the spectrum. In practice, these detectors are more sensitive than thermopiles and can readily detect the lower level blackbody emissions at these longer wavelengths to accuracies of 0.1 F. degree or better, depending on the observation (signal integration) time and the predetection bandwidth. While antenna size, and the attendant near-field, far-field limitation, can pose a problem in restricting the detection area to that of the eye, this can be overcome by making the maximum distance, from antenna to the eye (to be measured), several inches and by use of well known antenna approaches to providing a narrow beam. Even a 1-inch diameter parabolic dish antenna, for example, could have a far field beam width on the order of degrees and a focused near field that would encompass the animal or human's cornea area.

An antenna-detector-mixer device 41 may be implemented as a small integrated circuit. The antenna portion picks up the eye emissions at selected wavelengths, the mixer portion mixes the emission signal with the signal from oscillator 52, and the detector portion converts the emission signal to a lower frequency for amplification by amplifier 53. The antenna size and the oscillator frequency are functions of the desired emission wavelengths to be detected.

For all wavelengths (IR, millimeter, and micrometer), the detection of eyeball emissions at two or more wavelength bands offers the opportunity to minimize the effects of environmental temperature and background emission levels for a given temperature measurement. For example, signals at a first wavelength can be compared to signals from a second wavelength. For this implementation, the sensor unit 102 of FIG. 7 (or the antenna-mixer-detector 41 of FIG. 11) could be modified 10 to accommodate more than one emissions signal path or detector. This could be accomplished by the use of multiple filters and detectors. Alternatively, a single detector could be used, and a wheel or some other electromagnetic or electromechanical or magneto-optic device used to provide a succession of filters to that detector.

Figure 8:
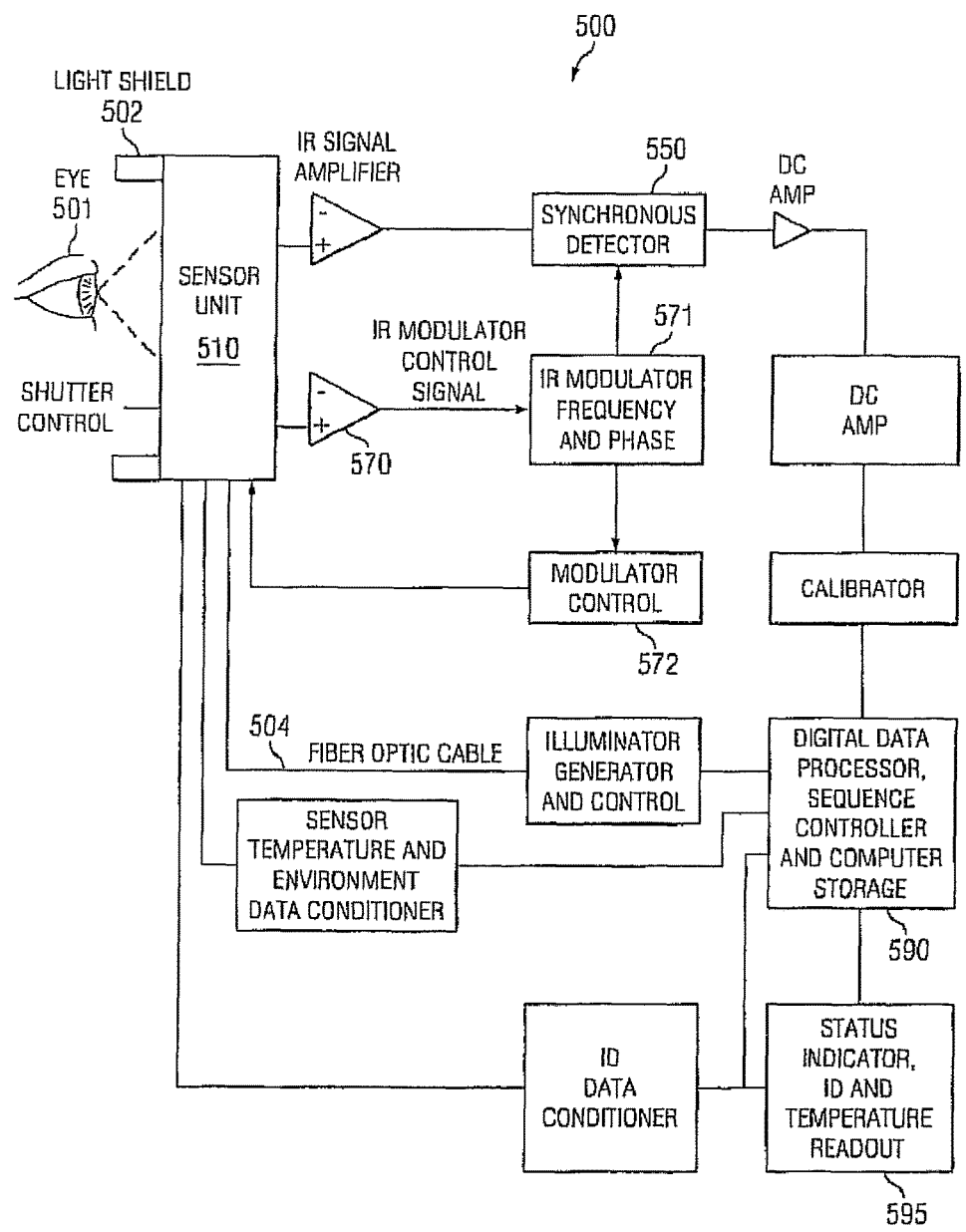
FIG. 8 is a block diagram of a second embodiment of an ocular thermometry instrument of the invention.

FIG. 8 is an improved embodiment of the invention, a temperature measurement device 500 for accurately and rapidly measuring core temperature. Device 500 is based on the use of internal eye emissions in the preferred spectral wavelength bands of 1600-1800 and/or 2150-2350 nm.

Figure 9:
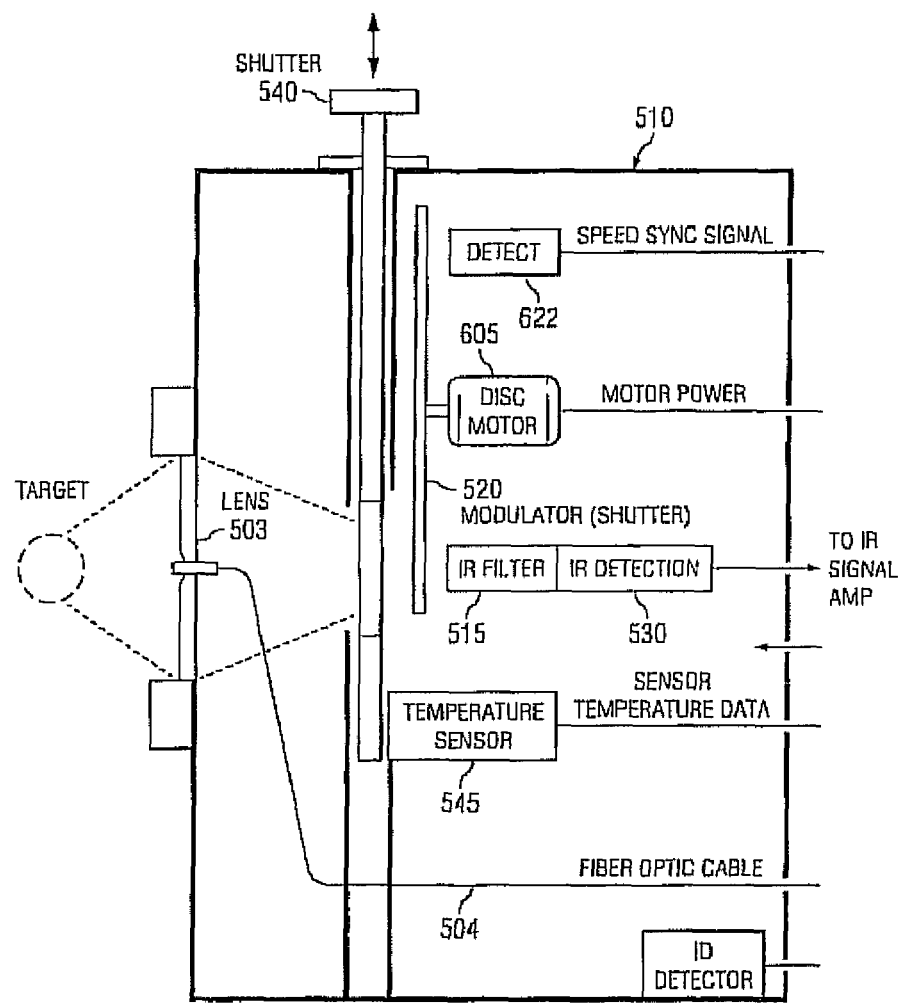
FIG. 9 shows details of the sensor unit 510 of FIG. 8.

FIG. 9 illustrates the sensor assembly 510 of FIG. 8 in further detail. An IR modulator 520 provides 25 amplitude modulation of the IR signal received by the IR detector 530 at a selected frequency generally in the range of 200 to 500

Hz. The output signal from the detector 530 has an AC component of the modulation frequency of amplitude proportional to the detected IR signal from the eye. This permits the use of more stable AC signal amplification and permits the use of synchronous detection and digital selection methods for improved sensitivity in detecting low intensity emissions. The modulator 520 may be implemented as a thin, dull black (emissivity-=1.00), opaque disc with slots or line of holes about a selected radius that is rotated at constant speed by a small motor 605. As the disc rotates the line of slots or holes alternately blocks or passes the IR emissions coming from the eye to the IR detector. The modulated input is also used by photo sensor 522 to optically generate a sync signal synchronized with the speed of motor 605 for use in accurately controlling the motor speed. This is performed using an amplifier 570, frequency and phase unit 571, and controller 572. Alternate means for implementing modulator 5200 may be used, such as vibrating elements such as a tuning fork tine, vibrating mirrors, optical switches, and others.

Referring to both FIGS. 8 and 9, sensor 500 also has a light shield 502, a rubber eyepiece to minimize any spurious light or IR from entering the eye sensing aperture 501. Lens 503 focuses the sensitive spot on the eye onto the IR detector 530. Light shutter 540 is normally closed but is opened manually or electromechanically, to pass IR emissions from the eye to the detector during eye temperature measurements. Bandpass filter 515 passes IR emissions of selected wavelengths from the eye to the detector 530. A precision digital temperature sensor 545 measures the temperature immediately adjacent to the shutter 540 prior to and during eye temperature measurements. An optical fiber 504 conducts visible blue light from a pulsed LED source located outside sensory assembly 510 (to minimize heating of sensor assembly 510) to the center of the lens 503. The open end of the optical fiber 504 protrudes through and is anchored to the center of the lens 503. This provides a low level light target for a person being tested as to where his eye needs to be focused for consistent measurements. For animals, this light tends to attract their attention and help hold the eye in the proper orientation for consistent measurements. This light should be of low level and low duty cycle to minimize any heating errors that could cause measurement errors and also must be of a wavelength that does not pass through the IR filter. To minimize the rate of temperature change in sensor assembly 510, it should be thermally isolated from the remainder of the instrument 500 to minimize the rate and magnitude of internal temperature changes from the environment and instrument power consumption.

Determining eye temperature using the embodiment of FIG. 8 is based on measuring and summing two components. The first component is the IR temperature based on the amplitude of the electrical voltage produced by the detected IR eye emissions as amplified by the electronic instrumentation. Synchronous detector 550 demodulates the signal using synchronous demodulation techniques. The IR signal voltage is corrected for any instrument zero offset as well as for any IR signal component that can arise from unequal IR modulator and shutter temperatures. The input signal is then converted to an equivalent IR temperature in the data processor 590 using a digitized calibration curve based on Planck's Law for the operating wavelengths and bandwidths and the instrument gain and calibration factors. The temperature from the corrected IR signal channel is then added to the temperature as measured by the shutter temperature sensor 545 to obtain the displayed or stored eye temperature. The temperature can be displayed in degrees F. or degrees C.

Shutter 540 may be closed for determining temperature from sensor 545, and then opened during acquisition of the measurement temperature from the eye. Processor 590 may be programmed to perform sequence controller functions for automatically operating shutter 540, or shutter 540 may be operated manually.

In a slightly different embodiment of FIG. 8, the modulator 520 operates at a near constant speed or rate, but to save on cost and weight of the device, no speed regulator and no synchronous detection are used. Various digital signal processing techniques may be used to recover the weak modulated IR signal in noise. This approach may not require as much hardware to implement, and could be more reliable.

Figure 12:
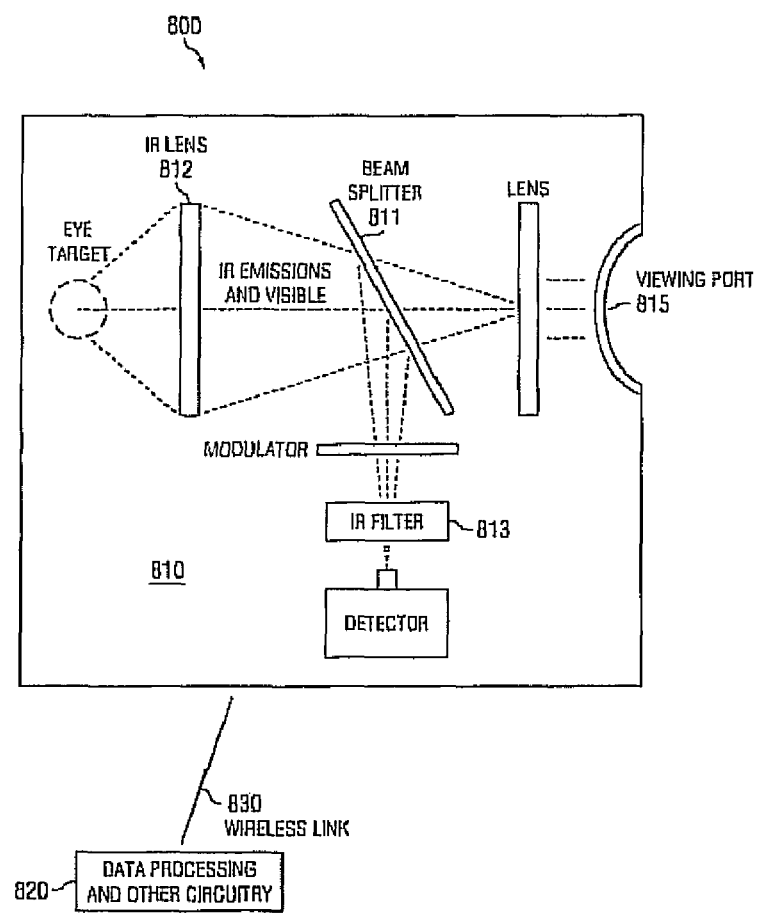
FIG. 12 illustrates an attachable embodiment 800 of the core temperature assessment system of the present invention.

FIG. 12 illustrates another embodiment, an attachable eye thermometer 800 for core temperature measurements, which is particularly useful for situations where a more compact instrument is desirable and particularly for use in temperature monitoring of patients that may be in surgery or confined to the bed and for animal temperature measurements. It would be particularly useful for attaching to an animal, or person, with a strap to hold the instrument in place over an eye. The previously described embodiments have been mostly intended for hand held measurements of temperature, and are well suited for this use, but the shape and length are less practical for attaching the device to a patient for monitoring over long periods. Device 800 is compact and may be relatively thin and is intended to fit over the eye region. An elastic material may be used to seal the periphery between the skin and the surface of the device 800 for fit and comfort as well as a barrier to external light which could cause errors. The change in configuration to achieve this embodiment is to bend the optical path of the IR emissions within the instrument and to possibly modify the overall instrument to have only the sensor assembly 810 in the attachable device. The sensor 810 communicates with the remainder of the instrument 820 over a wireless data link 830 or over a small cable and would be powered by an internal battery or over the data link cable. This embodiment bends the IR path by addition of a thin film optical beam splitter 811 between the lens 812 and the IR filter 813. This will reflect IR, of the critical wavelengths, at 90 30 degrees (+−) and allow the thickness of the package to be greatly reduced. In addition, by using a beam splitter that is transparent to visible light, it allows an optical viewing port 815 to be made available for viewing the eye through the beam splitter 811 and the lens 812. The optical port 815 can be optimized with additional optical components. The port 815 also is advantageous in allowing the operator or installer to properly align the sensor unit 810 with the desired region of the eye. In the embodiment of FIG. 12, the sensor unit 810 is like that of FIGS. 8 and 9, but could alternatively be implemented with other of the various configurations described above.

OTHER ALTERNATIVE TEMPERATURE ASSESSMENT MODULES. Although various embodiments of the core temperature assessment aspects of the invention are described herein, the scope of this element of the invention is not limited to these embodiments nor do alternative embodiments need to include all the features described herein. Other implementations could well be within the scope of this invention. In other embodiments, methods of the invention comprise application methods with one or more steps involving the thermometry system and the like that are involved in such largely conventional processes.

Such systems may also be utilized in ways that still fall within the scope of the invention.

Indeed, the core temperature assessment system of FIGS. 6-12 is just one core temperature assessment system usable in the herd management systems of FIGS. 1-5. It should be understood that much more basic temperature or other health condition indicators could be gathered and used in system and methods while still appreciating the advantages and benefits of the herd or patient management systems and methods that have been described or referenced elsewhere herein.

OVERALL SYSTEM AND METHOD ALTERNATIVES. Still other embodiments of the invention relate to products made by the described processes as well as apparatus for performing all or part of such processes. While there are many variations within the scope of the invention, one of ordinary skill in the art should consider the scope of the invention from a review of the claims appended hereto (including any amendments made to those claims in the course of prosecuting this and related applications) as considered in the context of the prior art and the various descriptions of this application.

It will be appreciated by those skilled in the art having the benefit of this disclosure that this invention provides a method for efficient management of livestock. It should also be understood that, rather than limiting the invention to cattle, alternative embodiments of broader aspects of the invention are adapted for use with any other ruminants, monogastrics and foul. As one such example, an alternative of the database correlation aspects of the present invention is embodied for use in collecting temperature data on human patients and correlating such data with numerous other data relating to such patients, including GPS coordinates, personal identity and health history, to enable predictive treatment of each such patient as well as future patients.

In some broad embodiments, aspects of the present invention provide a core-temperature-based herd management system for use in conjunction with features of other known herd management systems, techniques and methods and variations thereof. The present invention also envisions herd management systems and methods optimally adapted to convey tracking information through tags, while such tags also include information for further elaboration on data about each tagged member of the herd. Such systems and methods provide optimal design for ease-of-use, adaptation to robotic platforms, as well as applications within fields outside of the feeding environment, such as in milking, slaughtering and treatment applications.

Although the foregoing embodiments represent the most preferred at present, those of ordinary skill in the art will recognize many possible alternatives. For example, it may be possible to find another temperature or health assessment technique that works better than the particulars we have discussed. While the foregoing written descriptions enable one of ordinary skill to make and use what is considered presently to be best modes of the invention, those of ordinary skill will understand and appreciate the existence of variations, combinations, and equivalents of the specific embodiment, method, and examples herein.

It should be understood that the drawings and detailed descriptions herein are to be regarded in an illustrative rather than a restrictive manner, and are not intended to limit the invention to the particular forms and examples disclosed. To the contrary, the invention includes any further modifications, changes, rearrangements, substitutions, alternatives, design choices, and embodiments apparent to those of ordinary skill in the art, without departing from the spirit and scope of this invention, as defined by any claims included herewith or later added or amended in an application claiming priority to this present filing. The invention covers all embodiments within the scope and spirit of such claims, irrespective of whether such embodiments have been remotely referenced here or whether all features of such embodiments are known at the time of this filing. Thus, it is intended that the claims be interpreted to embrace all further modifications, changes, rearrangements, substitutions, alternatives, design choices, and embodiments that may be evident to those of skill in the art. In any case, all substantially equivalent systems, articles and methods should be considered within the scope of the present invention.

The present invention is just the answer for many of the unmet needs that have plagued the livestock industries—allowing efficient management of a herd based on quick assessment of core temperature in less than five seconds while each calf is in the chute. Other features also allow selective administration of appropriate antibiotics to calves categorized in subclinical and clinical symptom groups. Sorting and tagging the herd correspondingly further allows for practical control of various aspects of down stream management. The result enables not only early intervention for calves that actually need antibiotics, but also informed management of the overall herd based on objective standards. More importantly to the feedlot, the preferred embodiments enable increased feedlot profitability and potential cost savings.

Applicant is thought to have developed a reliable way to quickly, accurately and non-invasively measure core temperature in livestock, by passively detecting the amount of infrared energy coming out from inside the animal's eyes. They have demonstrated that an animal's eye offers great access to the core temperature via the optic artery at the rear of the eye, which connects directly to the core cerebral circulation of the brain. By focusing on the infrared wavelengths that are available from the interior of the eyeball, their technique targets the temperature within the eyeball and near the optic artery, without any significant interference from other sources or from common defects in the eye.

Current technology, using either digital or mercury thermometers, do not provide an accurate indication of core temperature. Rectal thermometer readings are one to three degrees below core temperature This difference is due to fecal material in the colon, lack of contact with the rectum due to gas pockets or simply failing to leave the thermometer in place long enough to get a rectal temperature. At the normal speed of processing, accurate temperature measurements are not made due to time constraints (i.e., 45 seconds using a digital thermometer, 1 minute using a mercury thermometer).

No known accurate, reproducible form of noninvasive measurement of body temperature, specifically core temperature exists. Non core body temperature measurements are less reflective of the body's true temperature. Core temperature is defined as the temperature of the heart and the brain. Currently, the "gold standard" technique to measure core temperature is the invasive placement of a right heart catheter or Swan-Ganz catheter. Current forms of noninvasive temperature measurement include oral, ear (tympanic), forehead (temporal artery sweep), skin temperature, rectal. Only two claim to measure core temperature (tympanic & temporal sweep).

These two forms of temperature measurement have attempted to measure core temperature in a noninvasive form but all have limited accuracy and difficulty obtaining reproducible measurements. These include tympanic or ear thermometers which have difficulty with accurate measurements due to anatomy of the ear canal, excess ear cerumen, excess hair in the canal, and operator error. The other form of measurement is via a swipe over the forehead and the temporal artery area of the forehead. This technique has difficulty with reproducible results and has a high potential for erroneous readings with operator error, sweat, cool skin, etc. Both of these techniques utilize infrared detection technology.

Still other embodiments of the invention relate to products made by the described processes as well as apparatus and systems for performing all or part of such processes. While there are many alternative variations, modifications and substitutions within the scope of the invention, one of ordinary skill in the art should consider the scope of the invention from a review of the claims appended hereto (including any amendments made to those claims in the course of prosecuting this and related applications) as considered in the context of the prior art and the various descriptions of this application.

Many other objects of the present invention will be evident from the remainder of this application in light of a more exhaustive understanding of the numerous difficulties and challenges faced by the prior art, which in turn will be evident to those skilled in the art.

The invention claimed is:

1. A method of managing a herd of animals for purposes of health evaluation and treatment, the method comprising:
   placing a number of animals serially in a manufactured livestock chute, the chute for restraining the animals;
   determining for each animal if the animal has a machine-readable identification tag thereon;
   if the animal does not have a machine-readable identification tag thereon, placing a machine-readable identification tag on the animal while in the chute;
   electronically receiving identification data from the animal's identification tag at an electronic data processor;
   measuring the core temperature of the animal while in the chute;
   electronically receiving an indication of the core temperature at the data processor, wherein the data processor is programmed to determine a health category for the animal based at least in part on the core temperature indication and to determine a dosing amount for medicinally treating the animal based at least in part on the core temperature indication;
   treating the animal in accordance with the dosing amount while in the chute;
   tagging the animal with one of a number of color codes, the color code corresponding to the health category of the animal;
   routing the animal from the chute to one of at least two holding pens based on the health category of the animal, each pen comprising a gate;
   electronically sending the dosing amount to medicine-delivering equipment associated with the holding pens; and
   reporting, by the data processor, of identification data and core temperature data of animals passing through the chute within specified time periods.

2. The method of claim 1, wherein the identification tag is an electronically readable identification tag.

3. The method of claim 1, wherein measuring the core temperature comprises using a non-invasive thermal detector for sensing the core temperature of the animal while in the chute.

4. The method of claim 3, wherein using a non-invasive thermal detector comprises positioning the thermal detector in front of an eye of the animal such that thermal radiation from within the eye is able to pass from the eye, wherein the detector comprises a hand-held housing, a power supply, circuitry, and a data transmitter; said housing having a window to allow passage of thermal radiation into an interior space of said housing; the window of said housing being positionable, through said window, and into said interior space of said housing; a thermal radiation transducer within said interior space, the thermal radiation transducer being adapted to generate transducer output corresponding to the thermal radiation passing into said interior space through said window; said circuitry being adapted to produce a core temperature signal based at least in part on the thermal radiation emitted from the eye of the animal.

5. The method of claim 1, further comprising treating the animal in accordance with the dosing amount while it is located in one of the pens.

6. The method of claim 1, wherein the chute comprises a gate.

7. The method of claim 1, wherein the chute is hydraulically-powered.

8. The method of claim 1, wherein the chute is adapted to weigh each animal.

9. The method of claim 8, wherein the data processor is programmed to determine the dosing amount for an animal based at least in part on the animal's weight.

10. The method of claim 1, wherein the identification tag is manufactured.

11. The method of claim 10, wherein the identification tag is machine encoded.

12. A method of managing a herd of animals for purposes of health evaluation and treatment, the method comprising:
    placing animals serially in a manufactured livestock chute, the chute for restraining the animals;
    determining for each animal if the animal has a machine-readable identification tag thereon;
    if the animal does not have a machine-readable identification tag thereon, placing a machine-readable identification tag on the animal while in the chute;
    electronically receiving identification data from the animal's identification tag at a data processor;
    measuring the core temperature of the animal while in the chute;
    electronically receiving an indication of the core temperature at the data processor, wherein the data processor is programmed to determine a health category for the animal based at least in part on the core temperature indication and to determine a dosing amount for medicinally treating the animal based at least in part on the core temperature indication;
    treating the animal in accordance with the dosing amount while in the chute;
    tagging the animal with one of a number of color codes, the color code corresponding to the health category of the animal;
    routing the animal from the chute to one of at least three holding pens based on the health category of the animal, each pen comprising a gate; and
    reporting, by the data processor, of identification data and core temperature data of animals passing through the chute within specified time periods.

13. The method of claim 12, wherein measuring the core temperature of the animal comprises using a non-invasive thermal detector for sensing the core temperature of the animal while in the chute.

14. The method of claim 13, wherein using a non-invasive thermal detector comprises positioning the thermal detector in front of an eye of the animal such that thermal radiation from within the eye is able to pass from the eye, wherein the thermal detector comprises a hand-held housing, a power supply, circuitry, and a data transmitter; said housing having a window to allow passage of thermal radiation into an interior space of said housing; the window of said housing being positionable in front of an eye of the animal such that thermal radiation from within the eye is able to pass from the eye, through said window, and into said interior space of said housing; a thermal radiation transducer within said interior space, the thermal radiation transducer being adapted to generate transducer output corresponding to the thermal radiation passing into said interior space through said window; said circuitry being adapted to produce a core temperature signal based at least in part on the thermal radiation emitted from the eye of the animal.

15. The method of claim 12, wherein the identification tag is electronically readable.

16. The method of claim 12, further comprising sending the dosing amount to medicine-delivering equipment associated with the holding pens.

17. The method of claim 16, further comprising treating the animal in accordance with the dosing amount while it is located in one of the pens.

18. A method of managing a herd of animals for purposes of health evaluation and treatment, the method comprising:
    placing animals serially in a manufactured livestock chute, the chute for restraining the animals;
    measuring the core temperature of each animal while the animal is in the chute;
    electronically receiving an indication of the core temperature at a data processor, wherein the data processor is programmed to determine a health category for the animal based at least in part on the core temperature indication and to determine a dosing amount for medicinally treating the animal based at least in part on the core temperature indication;
    treating the animal in accordance with the dosing amount while in the chute;
    tagging the animal with one of a number of color codes, the color code corresponding to the health category for the animal;
    routing the animal from the chute to one of at least three holding pens based on the health category of the animal, each pen comprising a gate;
    sending the dosing amount to medicine-delivering equipment associated with the holding pens; and
    reporting, by the data processor, of core temperature data of animals passing through the chute within specified time periods.

19. The method of claim 18, wherein measuring the core temperature of an animal comprises using a non-invasive thermal detector for sensing the core temperature of the animal while in the chute.

20. The method of claim 19, wherein using a non-invasive thermal detector comprises positioning the thermal detector in front of an eye of the animal such that thermal radiation from within the eye is able to pass from the eye, wherein the thermal detector comprises a hand-held housing, a power supply, circuitry, and a data transmitter; said housing having a window to allow passage of thermal radiation into an interior space of said housing; the window of said housing being positionable in front of an eye of the animal such that thermal radiation from within the eye is able to pass from the eye, through said window, and into said interior space of said housing; a thermal radiation transducer within said interior space, the thermal radiation transducer being adapted to generate transducer output corresponding to the thermal radiation passing into said interior space through said window; said circuitry being adapted to produce a core temperature signal based at least in part on the thermal radiation emitted from the eye of the animal.

21. The method of claim 18, further comprising:
    determining if the animal has an identification tag;
    if the animal does not have an identification tag, placing an identification tag on the animal while in the chute; and
    after determining that the animal has an identification tag or placing an identification tag if the animal does not have an identification tag, sending identification data to the data processor.

22. The method of claim 21, wherein the identification tag is an electronically readable identification tag.

23. The method of claim 18, further comprising treating the animal in accordance with the dosing amount while it is located in one of the pens.

24. A method of managing a herd of animals for purposes of health evaluation and treatment, the method comprising:
    placing animals serially in a manufactured livestock chute, the chute for restraining the animals;
    measuring the core temperature of each animal while the animal is in the chute;
    electronically receiving an indication of the core temperature at a data processor, wherein the data processor is programmed to determine a health category for the animal based at least in part on the core temperature indication and to determine a dosing amount for medicinally treating the animal based at least in part on the core temperature indication;
    treating the animal in accordance with the dosing amount while in the chute;
    tagging the animal with one of a number of color codes, the color code corresponding to the health category for the animal;
    routing the animal from the chute to one of at least three holding pens based on the health category of the animal, each pen comprising a gate; and
    reporting, by the data processor, of core temperature data of animals passing through the chute within specified time periods.

25. The method of claim 24, wherein measuring the core temperature of an animal comprises using a non-invasive thermal detector for sensing the core temperature of the animal while in the chute.

26. The method of claim 25, wherein using a non-invasive thermal detector comprises positioning the thermal detector in front of an eye of the animal such that thermal radiation from within the eye is able to pass from the eye, wherein the thermal detector comprises a hand-held housing, a power supply, circuitry, and a data transmitter; said housing having a window to allow passage of thermal radiation into an interior space of said housing; the window of said housing being positionable in front of an eye of the animal such that thermal radiation from within the eye is able to pass from the eye, through said window, and into said interior space of said housing; a thermal radiation transducer within said interior space, the thermal radiation transducer being adapted to generate transducer output corresponding to the thermal radiation passing into said interior space through said window; said circuitry being adapted to produce a core temperature signal based at least in part on the thermal radiation emitted from the eye of the animal.

27. The method of claim 24, further comprising:
determining if the animal has an identification tag;
if the animal does not have an identification tag, placing an identification tag on the animal while in the chute; and
after determining that the animal has an identification tag or placing an identification tag if the animal does not have an identification tag, sending identification data to a data processor.

28. The method of claim 27, wherein the identification tag is an electronically readable identification tag.

29. The method of claim 24, further comprising sending the dosing amount to medicine-delivering equipment associated with the holding pens.

30. The method of claim 29, further comprising treating the animal in accordance with the dosing amount while it is located in one of the pens.

* * * * *